(12) United States Patent
Rand et al.

(10) Patent No.: US 10,342,696 B2
(45) Date of Patent: Jul. 9, 2019

(54) PORTABLE RAPID COOLING, HYPOTHERMIA INDUCING HEADGEAR APPARATUS FOR TISSUE PRESERVATION

(71) Applicants: David Rand, Boca Raton, FL (US); William Rand, Boca Raton, FL (US); Felipe Echeverri, Coral Gables, FL (US)

(72) Inventors: David Rand, Boca Raton, FL (US); William Rand, Boca Raton, FL (US); Felipe Echeverri, Coral Gables, FL (US)

(73) Assignee: David Rand, Boca Raton, FL (US)

( * ) Notice: Subject to any disclaimer, the term of this patent is extended or adjusted under 35 U.S.C. 154(b) by 0 days.

(21) Appl. No.: 15/480,932

(22) Filed: Apr. 6, 2017

(65) Prior Publication Data

US 2017/0209306 A1 Jul. 27, 2017

Related U.S. Application Data

(63) Continuation of application No. 14/688,694, filed on Apr. 16, 2015, now Pat. No. 9,615,968.

(Continued)

(51) Int. Cl.
*A42B 1/00* (2006.01)
*A42B 1/22* (2006.01)
(Continued)

(52) U.S. Cl.
CPC .............. *A61F 7/106* (2013.01); *A42B 1/008* (2013.01); *A42B 1/22* (2013.01); *A61F 7/02* (2013.01);
(Continued)

(58) Field of Classification Search
CPC ...... A61F 2007/0002; A61F 2007/0007; A61F 2007/0008; A61F 7/106; A42B 1/008; A42B 3/285
See application file for complete search history.

(56) References Cited

U.S. PATENT DOCUMENTS 3,429,315 A * 2/1969 McDonald .............. A61F 7/106
 206/221
4,138,743 A 2/1979 Elkins et al.
(Continued)

FOREIGN PATENT DOCUMENTS

CN 2179017 Y 10/1994
CN 202407260 U 9/2012
(Continued)

OTHER PUBLICATIONS

"Cooling helmets may stabilize stroke patients", Retrieved on Jan. 28, 2015, from <http://www.webmd.com/stroke/news/20040205/cooling-helmets-may-stabilize-stroke-patients > (3 pages).
(Continued)

*Primary Examiner* — Kaitlyn E Smith
(74) *Attorney, Agent, or Firm* — Fox Rothschild LLP

(57) ABSTRACT

Hypothermic therapy headgear for patients includes a headpiece for engaging the head of the patient and a cooling member engaged to the headpiece for contacting at least one surface portion of the patient. The cooling member includes at least one cooling surface for contacting the surface portion of the patient, and at least two endothermic reaction components. The endothermic reaction components have an initial state where the endothermic reaction components are separated from contact with each other, and a treatment state in which the endothermic reaction components are placed into contact, wherein an endothermic reaction takes place and cools the cooling surface and the corresponding portion of the patient. An activation device selectively places the (Continued)

endothermic reaction components into the treatment state when a patient is in need of hypothermic therapy. A thermal therapy device and a method for administering thermal therapy are also disclosed.

17 Claims, 24 Drawing Sheets

Related U.S. Application Data

(60) Provisional application No. 61/980,357, filed on Apr. 16, 2014.

(51) Int. Cl.
*A61F 7/00* (2006.01)
*A61F 7/02* (2006.01)
*A61F 7/10* (2006.01)

(52) U.S. Cl.
CPC ........... *A61F 2007/0002* (2013.01); *A61F 2007/0008* (2013.01); *A61F 2007/0096* (2013.01); *A61F 2007/0268* (2013.01); *A61F 2007/0276* (2013.01)

(56) References Cited

U.S. PATENT DOCUMENTS

| | | | |
|---|---|---|---|
| 4,382,446 A | 5/1983 | Truelock et al. | |
| 4,551,858 A | 11/1985 | Pasternack | |
| 4,742,827 A * | 5/1988 | Lipton | A61F 7/02 607/109 |
| 4,753,242 A | 6/1988 | Saggers | |
| 4,765,338 A | 8/1988 | Turner et al. | |
| 4,776,042 A * | 10/1988 | Hanson | A42B 1/008 2/171 |
| 4,854,319 A * | 8/1989 | Tobin | A61F 7/10 2/171.2 |
| 4,891,501 A * | 1/1990 | Lipton | A61F 7/02 219/527 |
| 5,188,103 A * | 2/1993 | Smith | A61F 7/02 607/109 |
| 5,274,865 A * | 1/1994 | Takehashi | A47G 9/1036 5/421 |
| 5,395,400 A * | 3/1995 | Stafford | A42B 1/008 2/209 |
| 5,539,934 A * | 7/1996 | Ponder | A42B 3/285 2/413 |
| 5,950,234 A | 9/1999 | Leong et al. | |
| 6,183,501 B1 | 2/2001 | Latham | |
| 6,185,750 B1 * | 2/2001 | Dumas | A41D 13/0055 2/171.2 |
| 6,554,787 B1 * | 4/2003 | Griffin | A61F 7/02 601/70 |
| 7,083,839 B2 * | 8/2006 | Fish | A61F 7/03 428/35.7 |
| 7,930,772 B2 | 4/2011 | Fontanez | |
| 2003/0118779 A1 * | 6/2003 | Fish | A61F 7/03 428/168 |
| 2006/0005942 A1 * | 1/2006 | Griesbach, III | A61F 7/03 165/73 |
| 2007/0150033 A1 * | 6/2007 | Johnson | A61F 7/106 607/114 |
| 2009/0198311 A1 * | 8/2009 | Johnson | A61F 7/106 607/109 |
| 2010/0037366 A1 * | 2/2010 | Panicali | A42B 1/008 2/171.2 |
| 2010/0319110 A1 | 12/2010 | Preston-Powers | |
| 2010/0331752 A1 | 12/2010 | Cumming et al. | |
| 2012/0144555 A1 * | 6/2012 | Panicali | A42B 1/008 2/171.2 |
| 2012/0151664 A1 | 6/2012 | Kirshon | |
| 2013/0041439 A1 | 2/2013 | Gallagher | |
| 2013/0152274 A1 | 6/2013 | Welch | |
| 2013/0172829 A1 | 7/2013 | Badawi | |
| 2013/0174332 A1 | 7/2013 | Bryant et al. | |
| 2013/0211484 A1 | 8/2013 | Rozental | |
| 2013/0331914 A1 | 12/2013 | Lee et al. | |
| 2014/0130239 A1 | 5/2014 | Preston-Powers | |
| 2014/0216061 A1 * | 8/2014 | Paul | F25D 5/02 62/4 |
| 2014/0288624 A1 * | 9/2014 | Wasko | A61F 7/02 607/109 |
| 2014/0371828 A1 | 12/2014 | Whitely | |
| 2014/0379058 A1 | 12/2014 | Farrago et al. | |
| 2016/0030238 A1 * | 2/2016 | Foster | F25D 5/00 607/110 |

FOREIGN PATENT DOCUMENTS

| | | |
|---|---|---|
| EP | 0585353 A1 | 3/1994 |
| WO | 2009095690 A1 | 8/2009 |

OTHER PUBLICATIONS

"Diagram of Thermocrown", Retrieved on Jan. 28, 2015, from <http://www.thermopraxis.com/diagram.htm> (4 pages).
"Thermahelm", Retrieved on Jan. 28, 2015, from http://www.thermahelm.com/ (3 pages).
Thermopraxis: Our products, Retrieved on Jan. 28, 2015, from <hilp://www.thermopraxis.com/products.htm> (2 pages).

\* cited by examiner

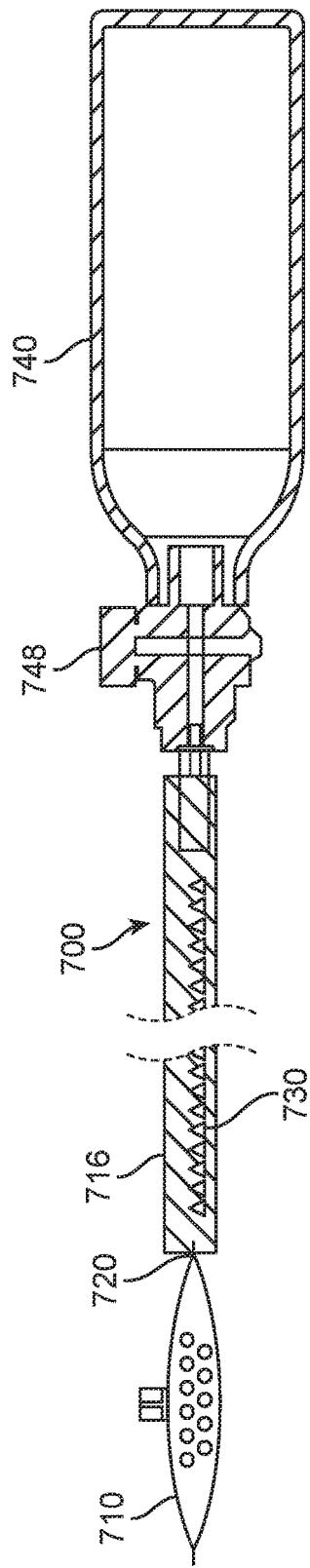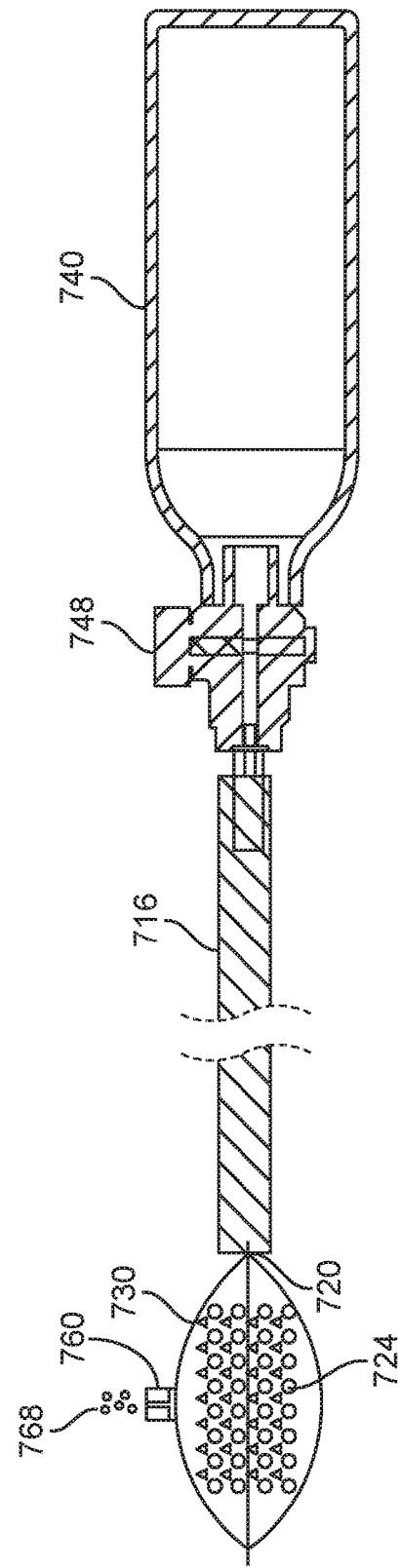

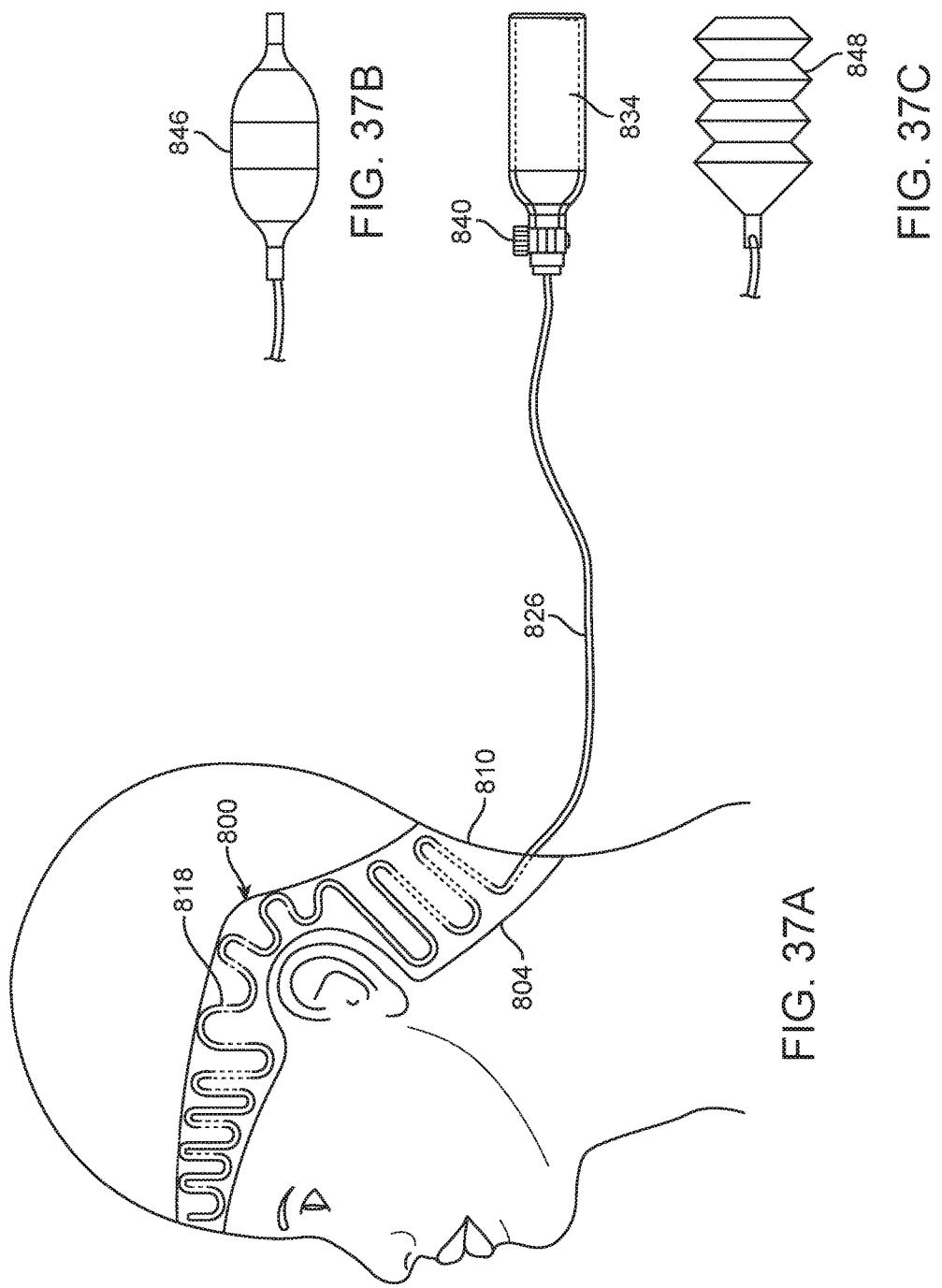

PORTABLE RAPID COOLING, HYPOTHERMIA INDUCING HEADGEAR APPARATUS FOR TISSUE PRESERVATION

CROSS-REFERENCE TO RELATED APPLICATIONS

This application is a continuation of U.S. application Ser. No. 14/688,694, filed on Apr. 16, 2015, now U.S. Pat. No. 9,615,968, which claims priority to and the benefit of U.S. Provisional Application No. 61/980,357 filed Apr. 16, 2014, the entireties of which are all incorporated herein by reference.

BACKGROUND OF THE INVENTION

Field of the Invention

The present invention relates generally to the field of emergency medical treatment. More specifically the present invention relates to an emergency medical device for delivering thermal therapy to a patient.

Description of Prior Art

In recent years doctors have recognized that the irreparable damage done to the tissues of the brain and brain stem following oxygen deprivation, such as from cardiac arrest, might be prevented by promptly and rapidly cooling these tissues to slow their metabolic rates until emergency care or further hypothermia treatment can be administered. Such thermal therapy is well known and there are many devices in existence for applying hypothermia thermal therapy.

One broad category of prior hypothermia devices is not readily hand portable, generally not suited to use outside a hospital setting and expensive is a cap or headgear which receives coolant through a tube from another apparatus. Examples of such devices are Lennox, et al., U.S. Pat. No. 7,052,509, issued on May 30, 2006 which is described as a method and device for rapidly inducing and then maintaining hypothermia; Lennox, et al., U.S. Pat. No. 6,962,600, issued on Nov. 8, 2005, for a method and apparatus for reducing body temperature of a subject; Lennox, U.S. Pat. No. 7,507,250, issued on Mar. 24, 2009, for a method and device for rapidly inducing hypothermia; Lennox, U.S. Pat. No. 7,008,445, issued on Mar. 7, 2006, for a method and device for rapidly inducing hypothermia; Lennox, et al., U.S. Pat. No. 8,454,671, Jun. 4, 2013, issued on Jun. 4, 2013, for a method and apparatus for reducing body temperature of a subject; and Klatz, et al., U.S. Pat. No. 5,913,885, issued on Jun. 22, 1999, for a brain cooling device and method for cooling; and Klatz et al., U.S. Pat. No. 6,277,143, issued on Aug. 21, 2001, for a brain cooling apparatus and method for cooling the brain.

Another broad category of hypothermia device is the hood or headgear having pockets into which cooling material or members are inserted. A problem with these devices is that the walls of the pockets are a permanent, reused part of the headgear and lack the thin flexibility needed to conform closely to all curves and irregularities of the wearer head, so that gaps are created between the cooling members and the wearer head. These gaps define heat insulating air pockets which inhibit and decidedly slow heat transfer and tissue cooling, when rapid and complete cooling is critical. An example of such a device is that disclosed in Zebuhr, et al., U.S. Pat. No. 4,172,495, issued on Oct. 30, 1979, which is described as a slurry-cooled headgear. Yet another broad category is a head cover contained in or forming part of a larger device or machine, an example of which is the one disclosed in Brader, U.S. Pat. No. 4,920,963, issued on May 1, 1990, for an apparatus for preventing brain damage during cardiac arrest, CPR or severe shock.

Other patents include Cummings, U.S. Pat. No. 8,262,601, issued on Sep. 11, 2012, for a headgear trauma bandage and method; Cummings, U.S. Patent Application Publication Number 2012/0296252, published on Nov. 22, 2012, for a head trauma bandage cap and method; Nambu, et al., U.S. Pat. No. 5,163,425, issued on Nov. 17, 1992, for a deformable cap for scalp cooling; Pasternack, U.S. Pat. No. 4,551,858, issued on Nov. 12, 1985, for protective headgear having a cooling harness; Brader, U.S. Pat. No. 8,449,590, issued on May 28, 2013, for an apparatus and method for preventing brain damage during cardiac arrest, CPR or severe shock; Maxted, et al., U.S. Pat. No. 5,342,411, issued on Aug. 30, 1994, for a scalp cooling device; Freedman, Jr., et al., U.S. Pat. No. 5,755,756, issued on May 26, 1998, for a hypothermia-inducing resuscitation unit; Tremblay, et al., U.S. Pat. No. 5,469,579, issued on Nov. 25, 1995, for a head cooling device; Pachys, U.S. Pat. No. 5,603,728, issued on Feb. 18, 1997, for a scalp cooling heating apparatus; Augustine, et al., U.S. Pat. No. 6,581,400, issued on Jun. 24, 2003, for an apparatus, system, and method for convectively and evaporatively cooling a head; Gunn, et al., U.S. Pat. No. 6,986,783, issued on Jan. 17, 2006, for a system and method for reducing brain injury particularly in newborn infants; Gunn, et al., U.S. Patent Application Publication Number U.S. 2002/0091431, published on Jul. 11, 2002, for a system and method for reducing brain injury particularly in newborn infants; Wass, U.S. Pat. No. 6,126,680, issued on Oct. 3, 2000, for a selective convective brain cooling apparatus and method; Radziunas, et al., U.S. Pat. No. 8,529,613, issued on Sep. 10, 2013, for an adjustable thermal cap; Bedford, U.S. Patent Application Publication Number 2006/0005291, published on Jan. 12, 2006, for a cooling headgear; Dow, U.S. Patent Application Publication Number 2012/0095538, published on Apr. 19, 2012, for a thermal wrap arrangement for applying heat/cold to the mandibular region of the head; Coba, U.S. Patent Application Serial Number 2009/0205107, published on Aug. 10, 2009, for cooling headgear; Gammons, et al., U.S. Patent Application Publication Number 2010/0106229, published on Apr. 29, 2010, for thermal skull pads for coolant system; and Stormby, U.S. Patent Application Publication Number 2012/0041526, published on Feb. 16, 2012, for head gear.

SUMMARY OF THE INVENTION

Hypothermic therapy headgear for patients includes a headpiece for engaging the head of the patient and a cooling member engaged to the headpiece for contacting at least one surface portion of the patient. The cooling member includes at least one cooling surface for contacting the surface portion of the patient, and at least two endothermic reaction components. The endothermic reaction components have an initial state where the endothermic reaction components are separated from contact with each other, and a treatment state in which the endothermic reaction components are placed into contact, wherein an endothermic reaction takes place and cools the cooling surface and the corresponding portion of the patient. An activation device selectively places the endothermic reaction components into the treatment state when a patient is in need of hypothermic therapy.

The headpiece can have an adjustable size. The headpiece can include an elastomeric portion. The headpiece can have an adjustable closure.

The cooling member can include at least one chamber for at least one of the endothermic reaction components, and a dividing member for separating the endothermic reaction component in the chamber from the at least one other endothermic reaction component. The activation device is operable to provide access through at least a portion of the dividing member to permit contact between the endothermic reaction components and cooling of the cooling surface and the corresponding portion of the patient.

The hypothermic therapy device can include a plurality of cooling members. The activation device can include a triggering device for opening a plurality of the dividing member of the cooling members. The triggering device can include a connector operable to open all of the dividing members with a single manipulation of the connector.

A liquid endothermic reaction component can be stored in a chamber located in an anterior portion of the cooling member. The activation member comprises a flexible activation surface, and wherein the application of a force to the flexible activation surface causes a portion of the dividing member to permit access and contact between the endothermic reaction components.

The activation member can include a compressed gas container and a valve for opening the container. Opening of the valve operates to apply fluid pressure to the dividing member and to permits contact of the endothermic reaction components through the dividing member. The compressed gas container is in fluid communication with at least one fluid channel when the valve is opened. One of the endothermic reaction components can be provided in the fluid channel, wherein entry of compressed gas from the compressed gas container into the fluid channel will drive that endothermic reaction component through the dividing member and into contact with the other endothermic reaction component in the chamber.

The hypothermic therapy headgear can further include a thermometer for providing an indication of the temperature of at least one of the cooling members. The hypothermic therapy headgear can include a timer. The timer can be activated by at least one selected from the group consisting of operation of the activation device and a temperature sensor.

The endothermic reaction components can be capable of cooling the cooling member to a temperature of less than 15° C. when activated. The endothermic reaction components can include ammonium nitrate, and the other of the endothermic reaction components can include at least one selected from the group consisting of barium hydroxide and water.

The headpiece can have earpieces for locating the headpiece on the users head. The cooling members can be positioned on the headgear such that when the headgear is positioned on the head of the patients the cooling members will contact at least one pulse point of the patient. The pulse points comprise at least one selected from the group consisting of the forehead, the base of the neck, and the temples.

A thermal therapy device for a patient can include a thermal member for contacting a surface portion of the patient. The thermal member can have at least one heat transfer surface for contacting the surface portion of the patient, and at least two thermal reaction components. The thermal reaction components have an initial state where the thermal reaction components are separated from contact with each other, and a treatment state in which the thermal reaction components are placed into contact, wherein a reaction takes place and heat transfer occurs between the reaction components, the heat transfer surface and the corresponding portion of the patient. Engagement structure retains the thermal member in contact with the surface portion of the patient. An activation device selectively upon demand places the thermal reaction components into the treatment state. The thermal member, the engagement structure and the activation device can be connected and the thermal therapy device is portable. The therapy can be hypothermic thermal therapy and the reaction of the thermal reaction components can be endothermic.

A method for administering hypothermic therapy to a surface portion of a patient includes the step of providing a cooling member comprising at least one cooling surface for contacting the surface portion of the patient, and at least two endothermic reaction components. The endothermic reaction components have an initial state where the endothermic reaction components are separated from contact with each other, and a treatment state in which the endothermic reaction components are placed into contact, wherein an endothermic reaction takes place and cools the cooling surface and the corresponding portion of the patient. An activation device is provided for selectively upon demand placing the endothermic reaction components into the treatment state. The activation device is operated to place the endothermic reaction components into contact with each other.

BRIEF DESCRIPTION OF THE DRAWINGS

Various other objects, advantages, and features of the invention will become apparent to those skilled in the art from the following discussion taken in conjunction with the following:

FIG. 35 is a schematic cross-section of an alternative embodiment of a pressurized cooling member design, in a first mode of operation.

FIG. 36 is a schematic cross-section in a second mode of operation.

FIGS. 37A, 37B and 37C are schematic side elevations of an alternative embodiment of headgear having coated fluid channels.

DETAILED DESCRIPTION OF THE INVENTION

Figure 1:
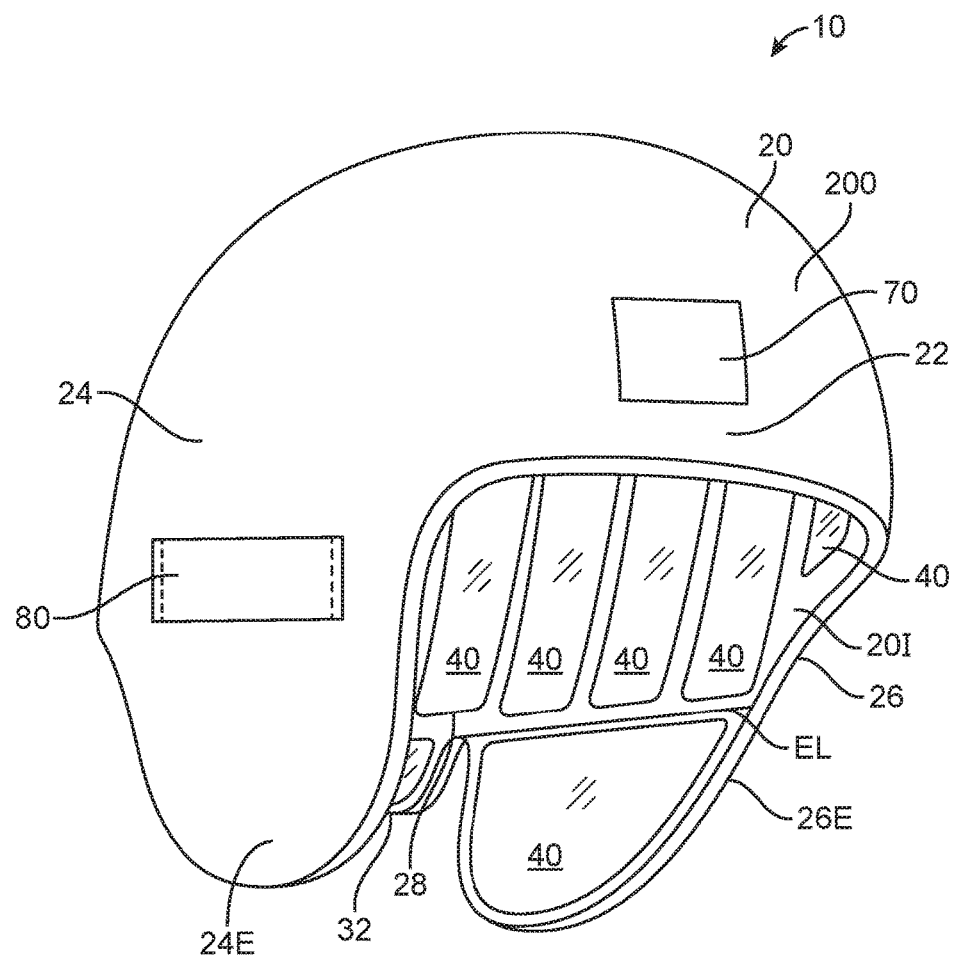
FIG. 1 is a perspective view of a first embodiment of the headgear.
Figure 2:
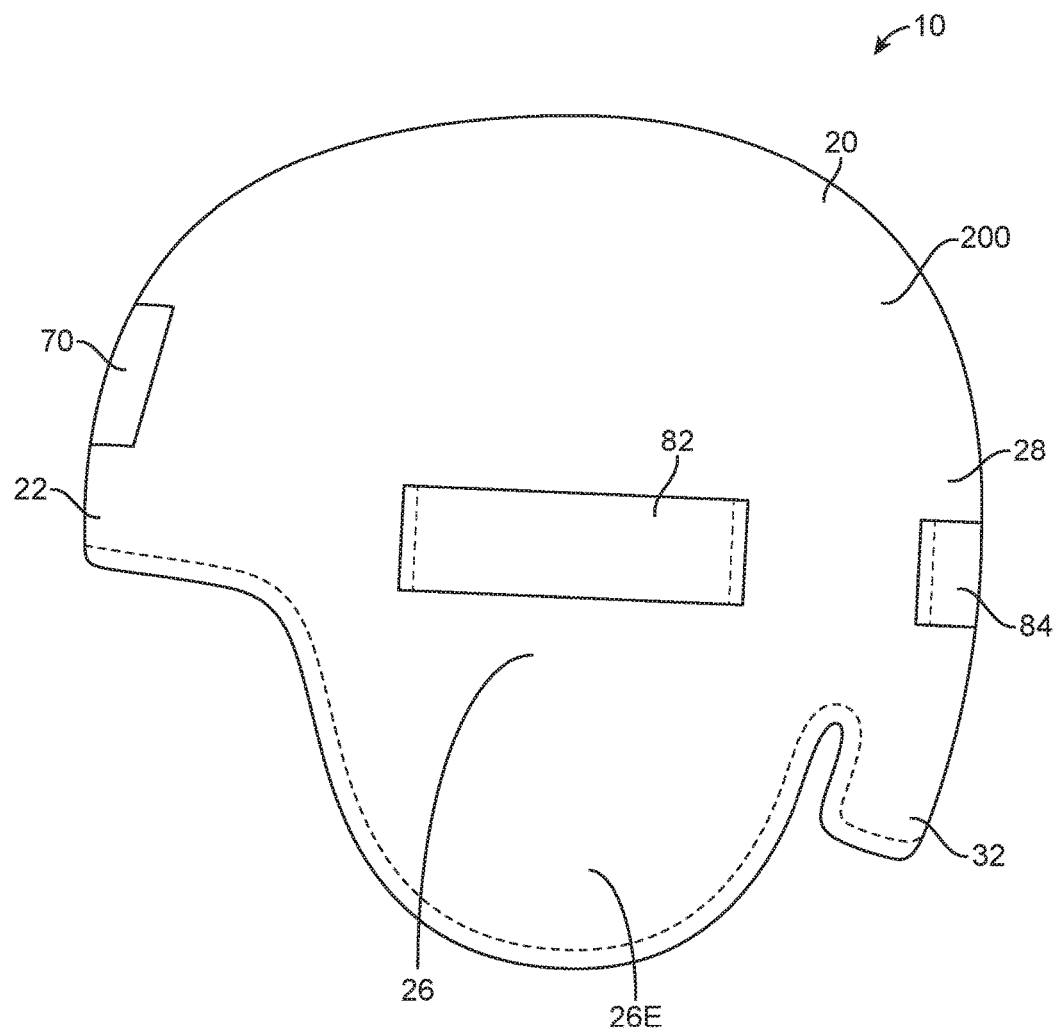
FIG. 2 a side elevation.
Figure 3:
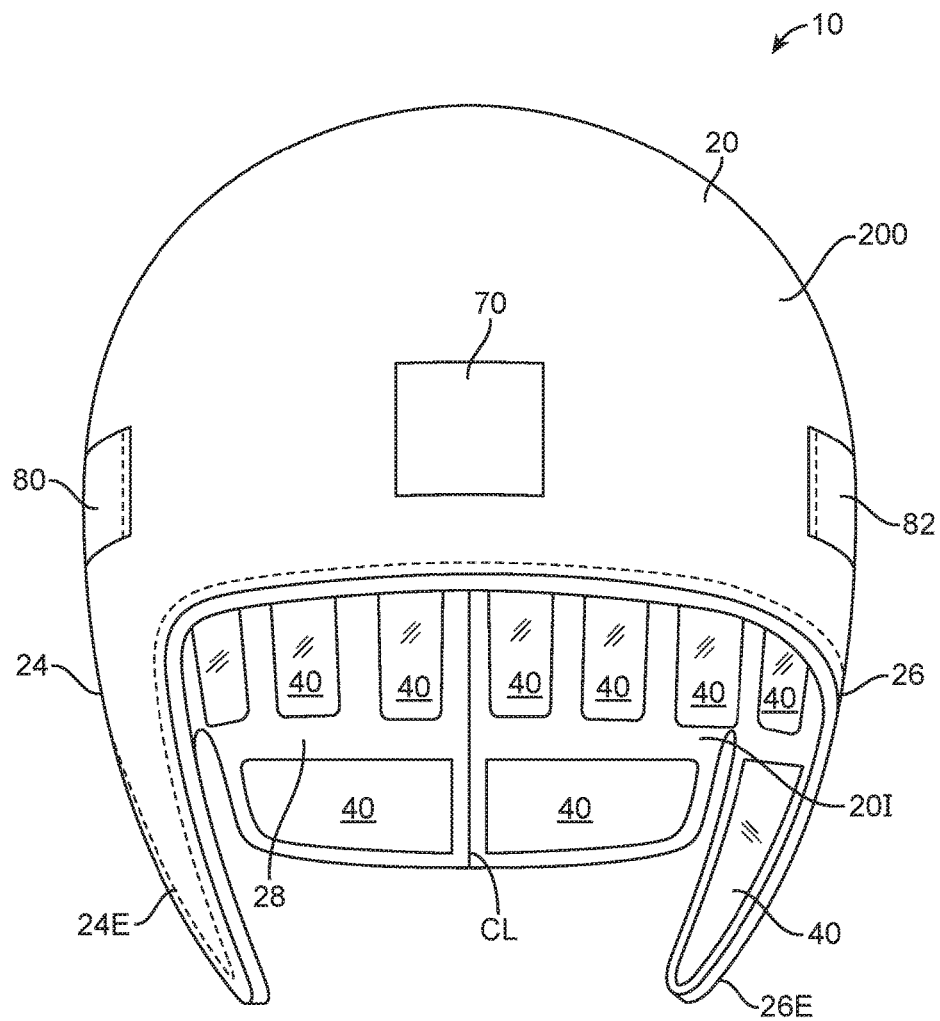
FIG. 3 is a front elevation.
Figure 4:
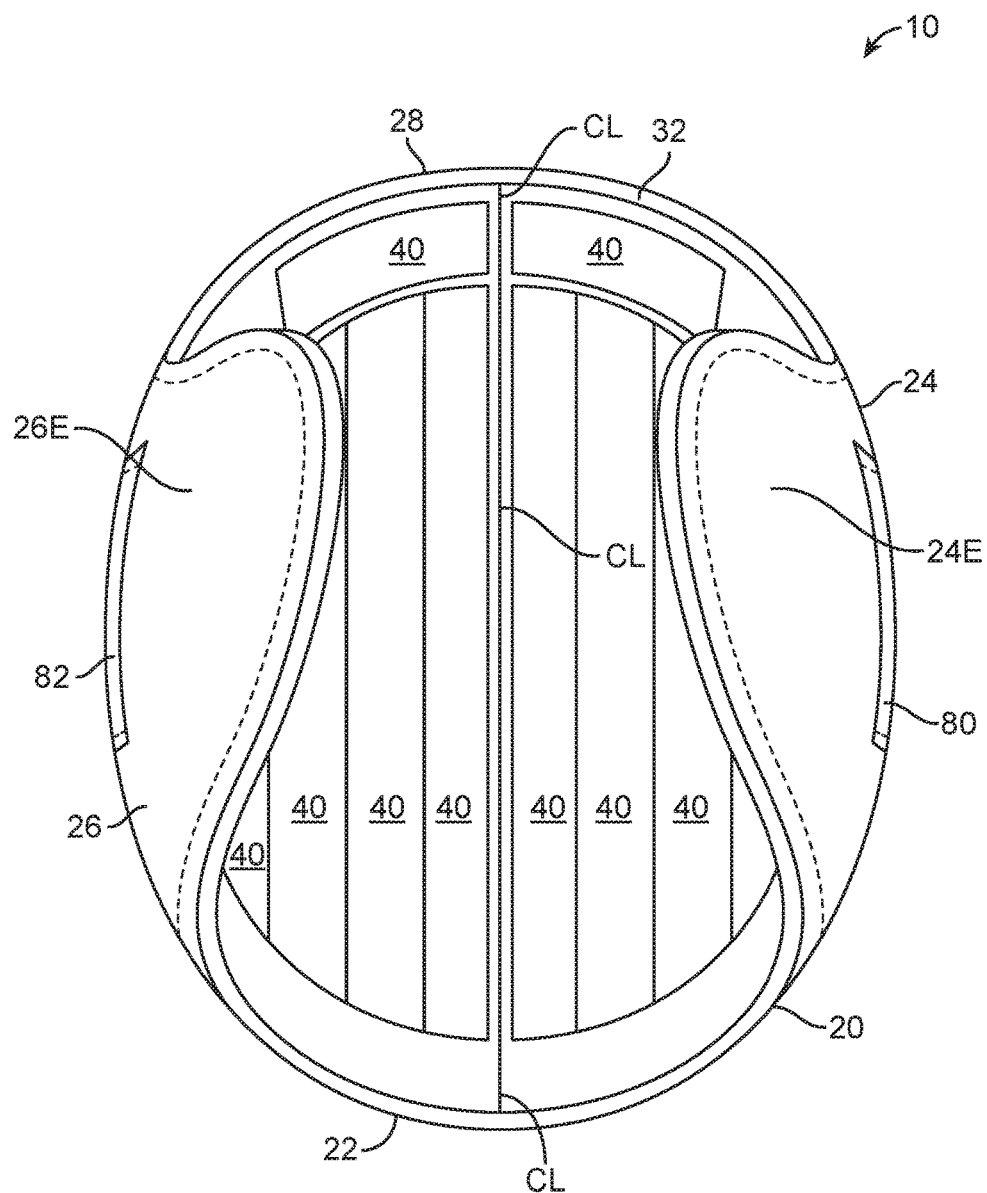
FIG. 4 is a bottom view.
Figure 5:
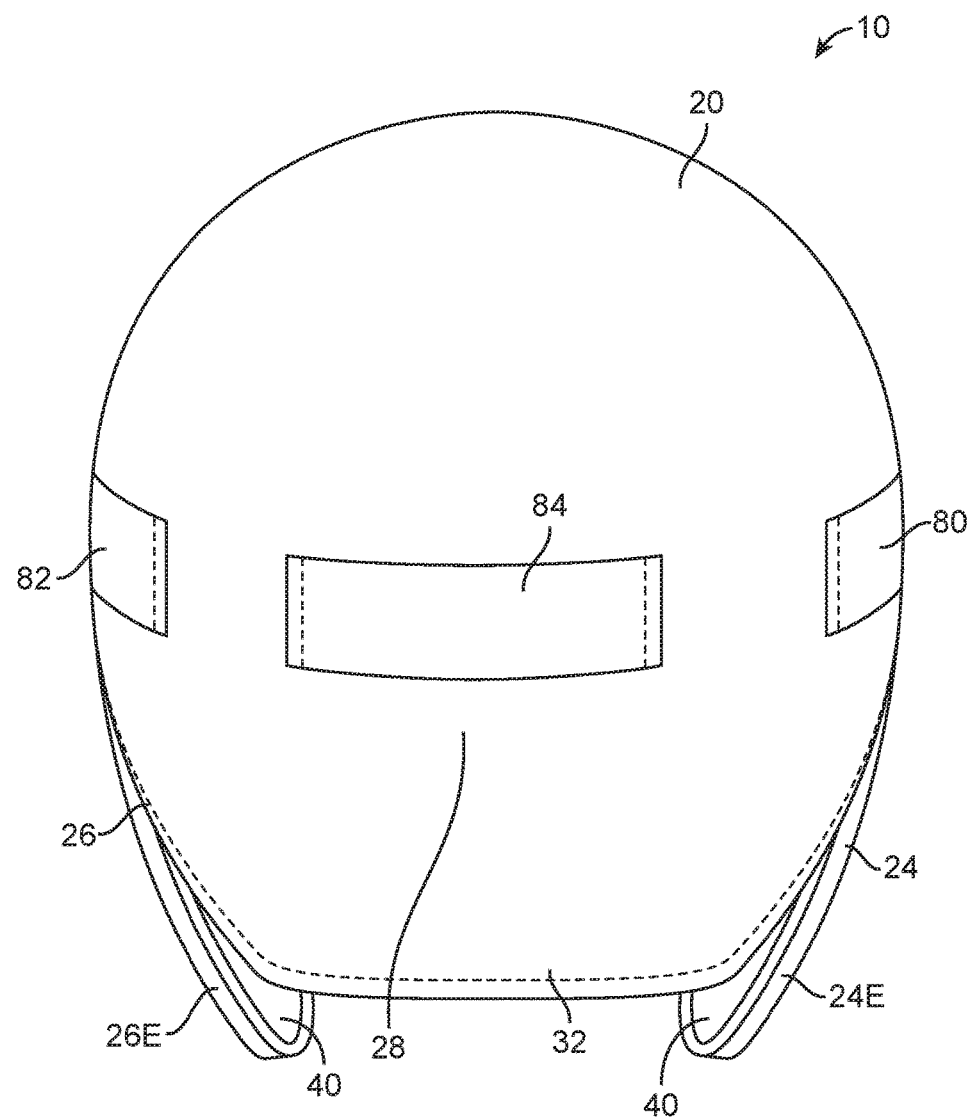
FIG. 5 is a rear elevation.
Figure 6:
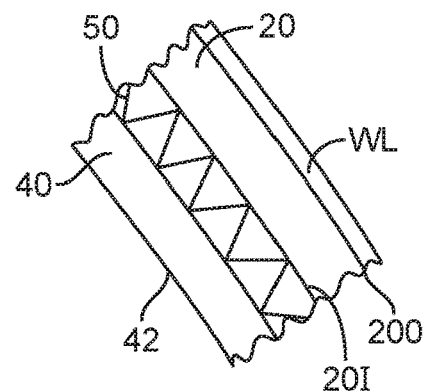
FIG. 6 is a cross section of the headgear.
Figure 7:
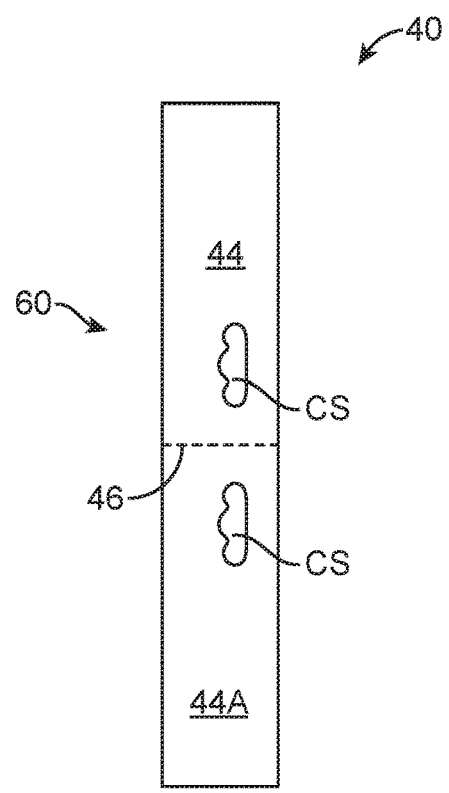
FIG. 7 is a schematic plan view of a cooling member, partially in phantom.

The present invention provides an emergency treatment headgear apparatus which induces hypothermia through rapid cooling for tissue preservation, and which is self-contained, not connected to any line and requires no other device in order to operate. The apparatus can be made readily and widely available outside a hospital setting to provide therapy at the very beginning of or during an insult to the brain, when damage can be prevented, rather than after the return of spontaneous circulation, that is when the heart restarts (ROSC) or when perfusion is reinstated, when tissues are likely to have been permanently damaged. The headgear apparatus readily folds substantially flat to store compactly and which can be opened and placed on the head of a patient quickly and easily without moving the patient. The headgear apparatus which can be activated in a single, quick action and is removed simply by pulling the apparatus off a patient head.

The coolant in one embodiment can be initially in a liquid state and the containment wall behind which the coolant is retained within the headgear is initially flexible and to conform closely to the curves and irregularities of a patient head for maximized heat transfer, whereupon the coolant rapidly solidifies and the coolant containment wall become fixed so that the interior of the headgear apparatus becomes a solid mold exactly fitting the wearer head. The reaction components themselves could solidify, for example in the case where water is one of the reaction components, the reaction product could be a solid, or freezable components such as gel which freezes at the temperatures produced by the reaction could be included in the cooling member.

The headgear apparatus can elevate the head of a patient resting on his or her back and to provide an optimal patient head position for intubation, and which minimizes head and neck trauma while the patient is being moved or is lying on his or her back.

The headgear apparatus does not interfere with other resuscitation efforts, including but not limited to oxygen placement, intubation, chest compression and electric shock. The headgear apparatus is easy for a single lay person to immediately understand, deploy and place on the head of a patient without delay, and is safe to use and relatively inexpensive to manufacture.

The headgear apparatus can be placed around the head of a person at the moment the person suffers oxygen loss to the brain and brain stem tissues, such as through a catastrophic loss of cranial blood flow, in order to cool and thereby lower the metabolic rate of the brain and brain stem, and thereby to preserve these tissues from irreparable damage until further hypothermia treatment can be administered, if necessary. Such a loss of blood flow and resultant oxygen deprivation to brain tissue can result from cardiac arrest, acute stroke, trauma, neonatal encephalopathy and from a variety of other conditions.

The headgear preferably is formed of a suitable flexible material such as nylon, polyvinylchloride (PVC) or polyurethane, to be readily collapsible for storage prior to use and to conform generally to the head of a wearer, and at least one and preferably several cooling members secured to the headgear inward surface. Cooling members each contain a rapid cooling and preferably rapid freezing substance, and each has a soft and thin inward member wall to conform closely to and fit snugly against the curves and irregularities of the individual wearer head. This close, conforming fit maximizes heat transfer. A layer of heat insulating material preferably is provided between the cooling members and the headgear inward surface or on the outward facing side of the cooling member which abuts the inward surface of the headgear to minimize the transfer of heat from the surrounding atmosphere into the cooling members. Different versions of the headgear apparatus may be provided which cool to different temperatures so that one most suitable for treatment of a given condition can be selected.

A cooling member activation device is provided which activates the rapid cooling substance such that the cooling member rapidly cools, preferably to a freezing temperature, while an optional gel substance simultaneously solidifies, such as through freezing, becoming a custom mold conforming to the individual wearer head. The activation device in one embodiment can activate several or all of the cooling members at the same time. The headgear and cooling members are configured to cover outer areas of the wearer head immediately adjacent to the brain and brain stem.

A non-slippery, waterproof lamination or layer, similar to that found on the outside surface of some soft foam coolers, can be provided over the exterior surface of the headgear to so that user hands do not slip on the outer surface of headgear or become wet, and additionally for cleanliness. The headgear preferably is provided in a flat configuration with one headgear side portion collapsed toward the other headgear side portion, permitting compact stacking of headgear assemblies while being stored or transported. The headgear preferably is initially wrapped in a headgear sealing envelope.

To make this headgear opening action easy to perform manually by a single person and particularly by a single lay person, first and second deployment side handles, respectively, are to be gripped in respective user hands to pull the side portions of the headgear apart in a fast, single action, to simultaneously activate the cooling members. Multiple cooling members preferably are placed edge to edge adjacent to each other along the headgear inward surface so that the headgear can preferably be secured to exterior surfaces of opposing side portions of the headgear. These handles are to be gripped in respective user hands to pull the side portions of the headgear apart in a fast, single action, to simultaneously activate the cooling members. Multiple cooling members preferably are placed edge to edge adjacent to each other along the headgear inward surface so that the headgear can flex and bend easily along lines between adjacent members for maximum headgear flexibility.

Hypothermic therapy headgear for patients includes a headpiece for engaging the head of the patient and a cooling member engaged to the headpiece for contacting at least one surface portion of the patient. The cooling member includes at least one cooling surface for contacting the surface portion of the patient, and at least two endothermic reaction components. The endothermic reaction components have an initial state where the endothermic reaction components are separated from contact with each other, and a treatment state in which the endothermic reaction components are placed into contact, wherein an endothermic reaction takes place and cools the cooling surface and the corresponding portion of the patient. An activation device selectively places the endothermic reaction components into the treatment state when a patient is in need of hypothermic therapy.

The headpiece can have an adjustable size. The headpiece can include an elastomeric portion. The headpiece can have an adjustable closure.

The cooling member can include at least one chamber for at least one of the endothermic reaction components, and a dividing member for separating the endothermic reaction component in the chamber from the at least one other endothermic reaction component. The activation device is operable to provide access through at least a portion of the dividing member to permit contact between the endothermic reaction components and cooling of the cooling surface and the corresponding portion of the patient.

The hypothermic therapy device can include a plurality of cooling members. The activation device can include a triggering device for opening a plurality of the dividing member of the cooling members. The triggering device can include a connector operable to open all of the dividing members with a single manipulation of the connector.

A liquid endothermic reaction component can be stored in a chamber located in an anterior portion of the cooling member. The patient will normally be supine, and in this position liquid and particulate reaction component in the anterior portion of the cooling member will flow with gravity to mix with the other reaction component. The activation member comprises a flexible activation surface, and wherein the application of a force to the flexible activation surface causes a portion of the dividing member to permit access and contact between the endothermic reaction components.

The activation member can include a compressed gas container and a valve for opening the container. Opening of the valve operates to apply fluid pressure to the dividing member and to permits contact of the endothermic reaction components through the dividing member. The compressed gas container is in fluid communication with at least one fluid channel when the valve is opened. One of the endothermic reaction components can be provided in the fluid channel, wherein entry of compressed gas from the compressed gas container into the fluid channel will drive that endothermic reaction component through the dividing member and into contact with the other endothermic reaction component in the chamber.

The hypothermic therapy headgear can further include a thermometer for providing an indication of the temperature of at least one of the cooling members. The hypothermic therapy headgear can include a timer. The timer can be activated by at least one selected from the group consisting of operation of the activation device and a temperature sensor.

Any suitable endothermic reaction components can be utilized. There are any suitable endothermic reaction components which can be separated and when mixed at room temperature and pressure, will create an endothermic reaction which will cool surrounding surfaces of the cooling member. The endothermic reaction components can be capable of cooling the cooling member to a temperature of less than 15° C. in a time of less than 3 minutes when activated. The endothermic reaction components can be selected to cool to alternative temperatures in alternative time periods depending on the application of the headgear. The endothermic reaction components can include ammonium nitrate, and the other of the endothermic reaction components can include at least one selected from the group consisting of barium hydroxide and water.

The headpiece can have cut outs for the ears. In addition to providing fit and comfort, these cut outs provide a point of reference for locating the headpiece on the patient's head so that the cooling members will be in the desired location. The cooling members can be positioned on the headgear such that when the headgear is positioned on the head of the patients the cooling members will contact at least one pulse point of the patient. The pulse points comprise at least one selected from the group consisting of the forehead, the base of the neck, and the temples.

A thermal therapy device for a patient can include a thermal member for contacting a surface portion of the patient. The thermal therapy can be applied to any external portion of the body. The thermal member can have at least one heat transfer surface for contacting the surface portion of the patient, and at least two thermal reaction components. The thermal reaction components have an initial state where the thermal reaction components are separated from contact with each other, and a treatment state in which the thermal reaction components are placed into contact, wherein a reaction takes place and heat transfer occurs between the reaction components, the heat transfer surface and the corresponding portion of the patient. Engagement structure retains the thermal member in contact with the surface portion of the patient. An activation device selectively upon demand places the thermal reaction components into the treatment state. The thermal member, the engagement structure and the activation device can be connected and the thermal therapy device is portable. The therapy can be hypothermic thermal therapy and the reaction of the thermal reaction components can be endothermic. The therapy can alternatively be heating.

A method for administering hypothermic therapy to a surface portion of a patient includes the step of providing a cooling member comprising at least one cooling surface for contacting the surface portion of the patient, and at least two endothermic reaction components. The endothermic reaction components have an initial state where the endothermic reaction components are separated from contact with each other, and a treatment state in which the endothermic reaction components are placed into contact, wherein an endothermic reaction takes place and cools the cooling surface and the corresponding portion of the patient. An activation device is provided for selectively upon demand placing the endothermic reaction components into the treatment state. The activation device is operated to place the endothermic reaction components into contact with each other.

Referring to FIGS. 1-5, an emergency treatment headgear apparatus 10 lined with a contained rapid cooling substance CS is disclosed for placement around the head of a person at the moment the person suffers oxygen deprivation to the brain and brain stem such as through a catastrophic loss of cranial blood flow, in order to cool and thereby lower the metabolic rate of the brain and brain stem, and thereby to preserve these tissues from irreparable damage until further hypothermia treatment can be administered, if necessary. Such a loss of blood flow and resultant oxygen deprivation can result from cardiac arrest, acute stroke, trauma, neonatal encephalopathy and from a variety of other conditions.

The apparatus 10 preferably includes a headgear 20 formed of a flexible material such as nylon, PVC or polyurethane, to be readily collapsible for storage prior to use and to conform generally to the head of a wearer, and at least one and preferably several cooling members 40 secured to the headgear inward surface 20 I. Cooling members 40 each contain a rapid cooling and preferably rapid freezing substance CS, and each has a soft and thin inward member wall 42 to conform closely to and fit snugly against the curves and irregularities of the individual wearer head. This close, conforming fit maximizes heat transfer, because it maximizes direct contact between the cooling members 40 and the wearer head, so that heat transfers from the wearer head into the cooling members 40 through the highly efficient mechanism of conduction rather than through the highly inefficient mechanism of radiation across a gap or void. It is preferred that a heat insulating layer 50 formed of heat insulating material or an insulating structure such as a resilient corrugated sheet be provided between the headgear 20 and the cooling members 40. Alternatively, the insulating layer 50 may be provided on the outward surface of headgear 20.

It is contemplated that several versions of headgear apparatus 10 may be provided which produce different cooling temperatures so that an apparatus temperature can be selected which is suitable for the condition being treated. For example, a condition treated with hypothermia is neurogenic fever. It is also preferred that apparatus not include any structures of metal or other material that could conduct electricity from an electric shock administered during resuscitation.

Cooling member activation means 60 are provided which activates the rapid cooling substance CS such that the cooling member 40 rapidly cools, preferably to a freezing temperature, while the substance CS simultaneously solidifies, such as through freezing, becoming a custom mold M conforming to the individual wearer head. The headgear 20 and cooling members 40 are configured to cover outer areas of the wearer head immediately adjacent to the brain and brain stem. A timer 70 preferably is provided in the form of a patch of material which progressively changes color after activation and which is activated automatically upon activation of the cooling members 40. This alerts doctors at a treatment center receiving the wearer to the length of time hypothermia therapy has been administered which may reflect (in a witnessed event) the length of time elapsed since the initial loss of spontaneous circulation.

The headgear 20 includes a headgear front portion 22, which covers the wearer forehead, a first side portion 24 which covers a first side of the wearer head, a headgear second side portion 26 which covers a second side of the wearer head, and a back portion 28 which covers the back of the wearer head. The first side portion 24 includes a first ear covering section 24E and the second side portion 26 includes a second ear covering section 26E covering corresponding wearer ears, respectively, ear covering sections preferably taking the form of downwardly protruding and rounded ear flaps 24E and 26E. Ear flaps 24E and 26E are designed specifically not to interfere with procedures requiring access to the area of the ears, such as the placement of oxygen masks. The ear flaps 24E and 26E are further designed to be easily lifted and to fall back into their initial ear covering positions when released so that they continue to cover that area of the brain. Cooling members 40 are provided on the inward surfaces of the ear flaps 24E and 26E, and are separate from cooling members 40 mounted in the remainder of the headgear 20 to leave a gap along the bending upper region of the flaps 24E and 26E. As a result, the ear flaps 24E and 26E easily can be bent along an ear flap bending line EL and lifted upwardly without bending any cooling members 40. The back portion 28 preferably includes a rear sealing skirt section 32 which extends a certain distance, such as but not limited to 5 centimeters below the rear lower edge of the cooling member or members 40 lining back portion 28. The rear sealing skirt portion 32 preferably contained elastic to pivot and rest against the wearer neck and obstruct air from entering the headgear 20 warming an adjacent cooling member 40. A non-slippery, waterproof lamination or layer WL, similar to that found on the exterior surface of some soft foam coolers, preferably is provided over the headgear outward surface 200 to so that user hands do not slip on the outer surface of headgear 20 or become wet, and additionally for cleanliness.

The headgear 20 preferably is provided in a flat configuration with one headgear side portion 24 collapsed toward the other headgear side portion 26, permitting compact stacking of headgear assemblies 10 while being stored or transported. The headgear 20 preferably is initially wrapped in a headgear sealing envelope. The headgear sealing envelope preferably is made of an inexpensive and biodegradable material such as a suitable plastic to be readily disposable. The envelope preferably is transparent so that the headgear 20 is clearly visible within the envelope and any use instructions appearing on the headgear 20 are clearly visible even before the envelope is opened. Use instructions preferably are also or alternatively printed on the envelope itself.

The headgear back portion 28, which fits against the back of a wearer head, is optionally of greater thickness than the rest of the headgear 20 so that the head of a wearer, lying on his or her back, is elevated to a medically optimized angle for intubations such as the placing of a breathing tube into the wearer airway and also for minimizing stress on the neck. The headgear 20 preferably is provided in child, infant and adult sizes to closely fit any head, the headgear 20 conforming to variations in head sizes and shapes within these categories as a result of its flexibility.

To make this headgear 20 opening action easy to perform manually by a single person and particularly by a single lay person, first and second deployment side handles 80 and 82, respectively, preferably are secured to exterior surfaces 20E of opposing side portions 24 and 26 of the headgear 20. These handles 80 and 82 are to be gripped in respective user hands to pull the side portions 24 and 26 of the headgear 20 apart in a fast, single action, to simultaneously activate the cooling members 40. A back handle 84 preferably is provided on the outer back surface of the headgear for additional help in pulling the headgear 20 onto the wearer head. The handles 80-84 simply can be grabbed, or alternatively user fingers or hands can be slid through or into them. The user also uses handles 80 to maneuver the headgear 20 around and onto the wearer head so that the headgear 20 is properly seated. Proper seating of the headgear 20 in most instances can be determined by feel, because the headgear 20, when properly seated, resists further movement on the wearer head. The handles 80 preferably are horizontal straps which rest flat against the sides 24 and 26 of the headgear 20 prior to use, under which, as noted, a user easily fits his or her fingers to quickly grip and pull the headgear apart to the appropriate anatomical position.

Multiple cooling members 40 preferably are placed edge to edge adjacent to each other along the headgear inward surface 201 so that the headgear 20 can flex and bend easily along lines between adjacent members 40 for maximum headgear 20 flexibility. Rows of members 40 preferably meet along a central fold line CL extending from the front to the back of the headgear 20 to permit the headgear apparatus 10 to fold easily and fully along the central fold line CL, the first and second headgear side portions 24 and 26 collapse toward each other. The member or members 40 preferably are secured within the headgear 20 by sewing them to the headgear inward surface 201 along their edges, or with opposing hook and loop fastener pads (not shown) adhesively bonded to cooling members 40 and sewn to the headgear inward surface 201. The cooling member activation means 60 preferably takes the form of a trigger assembly activated automatically by opening the sealing envelope HE, and alternatively by spreading apart the headgear side portions 24 and 26 as the headgear 20 is opened for use. Alternatively, a trigger assembly may be provided which is activated through spreading the handles 80-84, which in turn may be attached to an elastic cord connected to the headgear 20 that triggers activation of the cooling members 40. Thus, in a fast, single and simultaneous action, the user opens the headgear 20 and activates the cooling members 40, simply by pulling the side portions 24 and 26 of the headgear 20 apart from each other or by spreading the handles 80-84. Other contemplated easy to use trigger assemblies 60 include a rip cord.

The rapid cooling substance CS preferably takes the form of a gel. The gel CS can be activated with the cooling member activation means 60 in any of a variety of ways. The gel CS components within each cooling member 40 initially may be retained in member compartments 44 and 44A separated by a membrane 46, so that operation of the cooling member activation means 60 breaks the membrane 46 the gel CS components mix to initiate cooling.

Treatment with the apparatus 10 normally is initiated when no pulse is detected a person. Simple operating instructions preferably are provided on the headgear 20 itself, whether in the form of words or illustrative sketches of the deployment and fitting steps, or both. It is contemplated that apparatus 10 would be mounted at designated locations along walls of buildings such as airport terminals, much as fire extinguishers are now mounted and displayed, with each location and apparatus 10 having conspicuous, standardized markings to be seen and recognized easily. Just as it has become common knowledge that CPR is started when the patient is unresponsive with no pulse which is easy to detect, so too the use and the criticality of use of the apparatus 10 can be explained and can become common knowledge.

Figure 8:
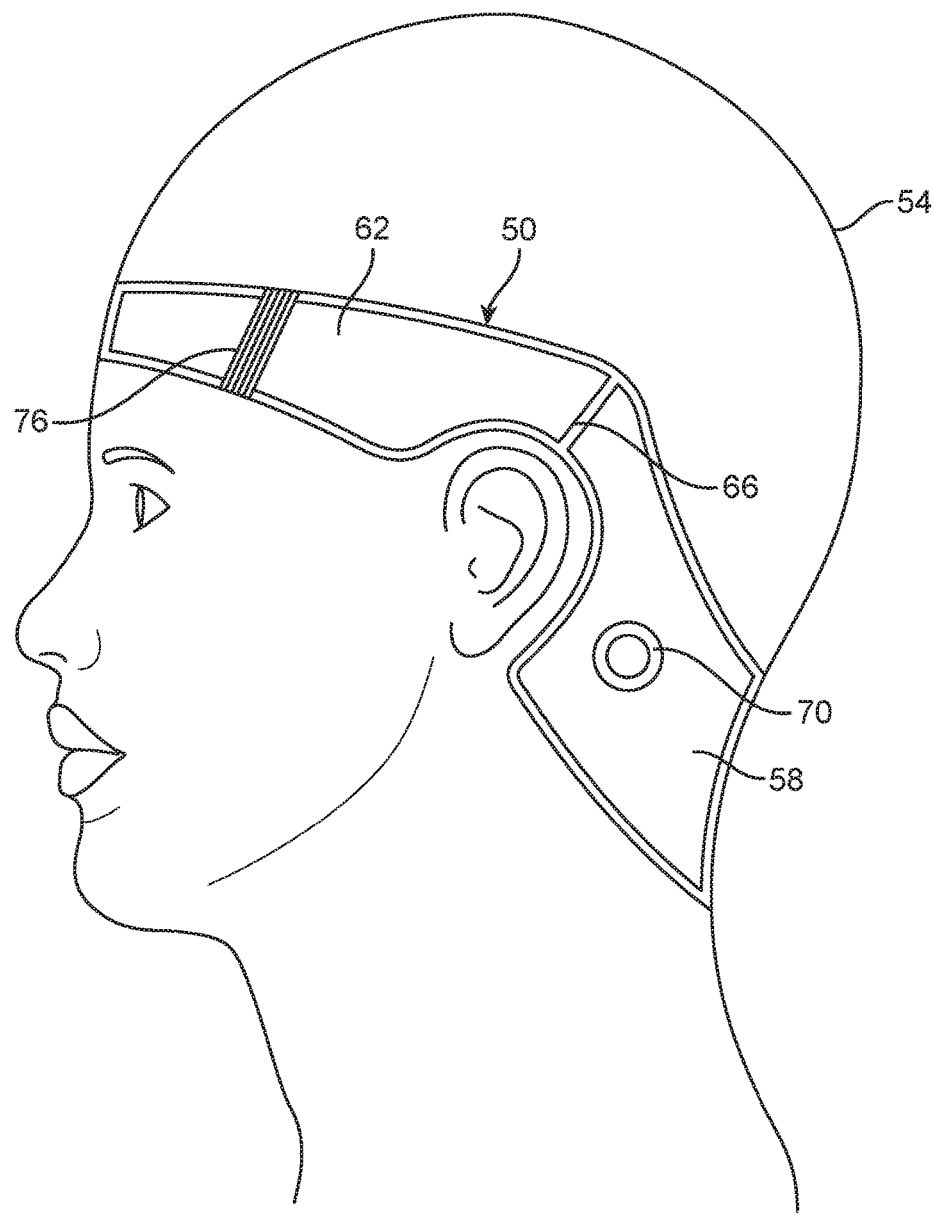
FIG. 8 is a side elevation of a second embodiment.
Figure 9:
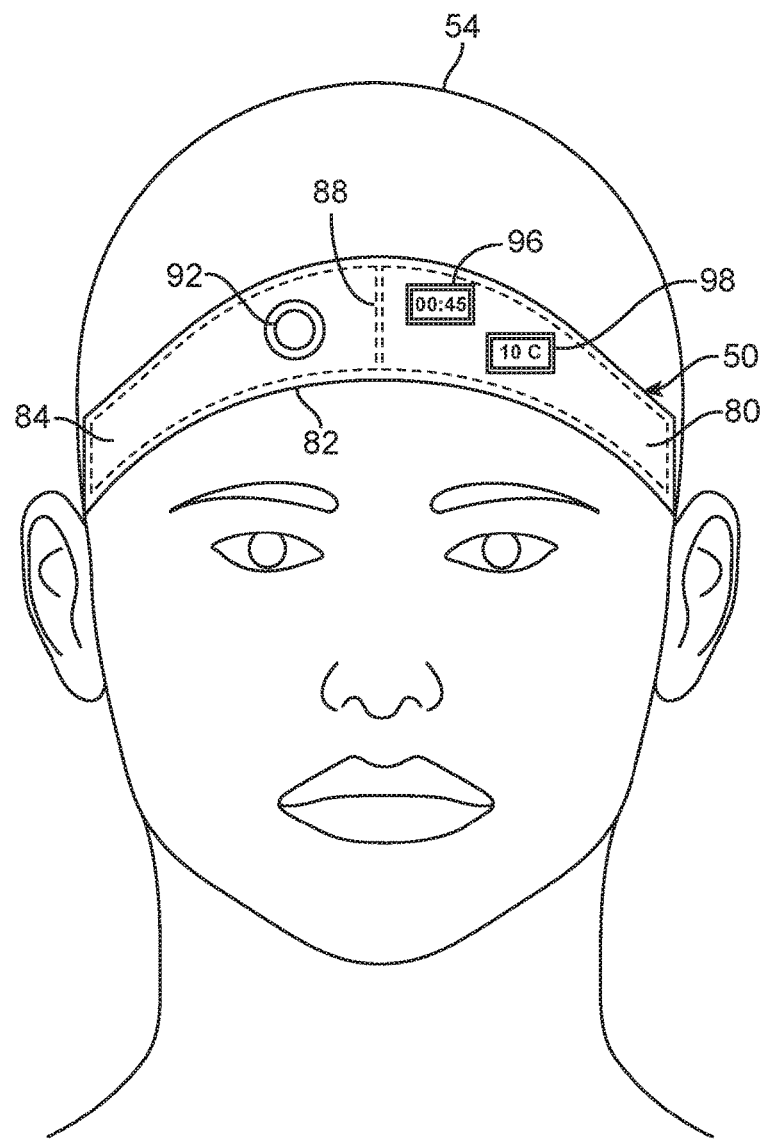
FIG. 9 is a front elevation.
Figure 10:
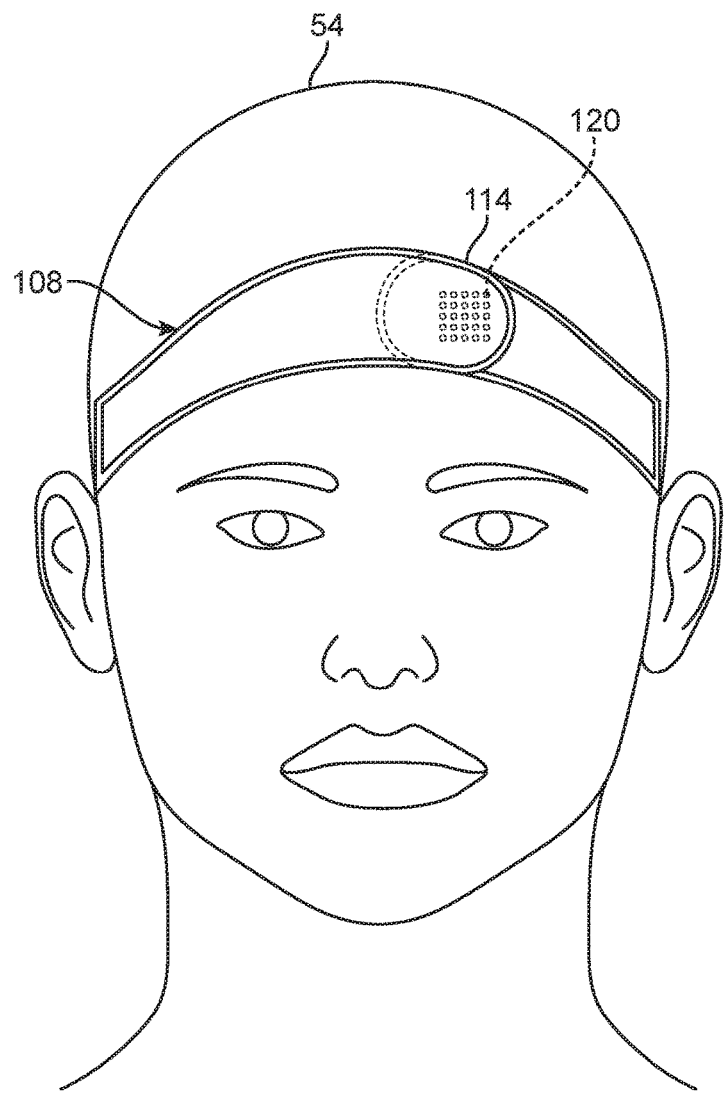
FIG. 10 is a front elevation of the second embodiment with an adjustable closure.

There is shown in FIGS. 8-10 an alternative headgear 50 provided on a head 54 of the patient. The headgear 50 is generally in the shape of a loop for securing to the head 54. A portion 58 covers the base of the neck and forehead portion 82 supplies a cooling member to the forehead. Cooling members are secured in location so as to cool these pulse points of the patient. A dividing member 66 can be applied to separate compartments 62 and 58 which include different endothermic reaction components. A flexible portion 70 can have indicia to inform the user where to apply pressure. The applied pressure will create a rise in internal fluid pressure within chamber 58 and cause the dividing member 66 to permit access between the compartments in the endothermic reaction to proceed. The dividing member 66 is modified under pressure to permit the passage of the reaction components and thereby to permit contact and the endothermic reaction to occur. Forehead portion 82 can have first and second compartments 80 and 84, respectively separated by a dividing member 88. A flexible portion 92 can be used to apply pressure which creates fluid pressure within chamber 84 to apply pressure to the dividing member 88 and permit access between the compartments 80 and 84. Other constructions for the dividing member are possible.

The headgear 50 can be made adjustable to fit different size heads 54. One or more elastic portions 76 can be provided to facilitate adjustability. A timer 96 can be provided to generate an indication of the length of time that has elapsed since hypothermic therapy started. The timer 96 can be activated by the user, by some connection to the activation device, or by a thermal sensor and switch. The timer can be electronic, or can be materials which progressively change color after initial mixing at the moment of apparatus deployment and thereby provide an indication of lapsed time. A thermometer 98 can be provided to provide an indication of the temperature of the cooling member. This alerts doctors at a treatment center receiving the wearer to the length of time hypothermia therapy has been administered, which may reflect (in a witnessed event) the length of time elapsed since the initial loss of spontaneous circulation.

An alternative embodiment of headgear 108 is shown in FIG. 10. The headpiece 108 is made adjustable by an adjustable closure 114 having hook and loop fastener 120. Other constructions for providing size adjustability to the headpiece such as buckles, buttons and the like are possible.

Figure 12:
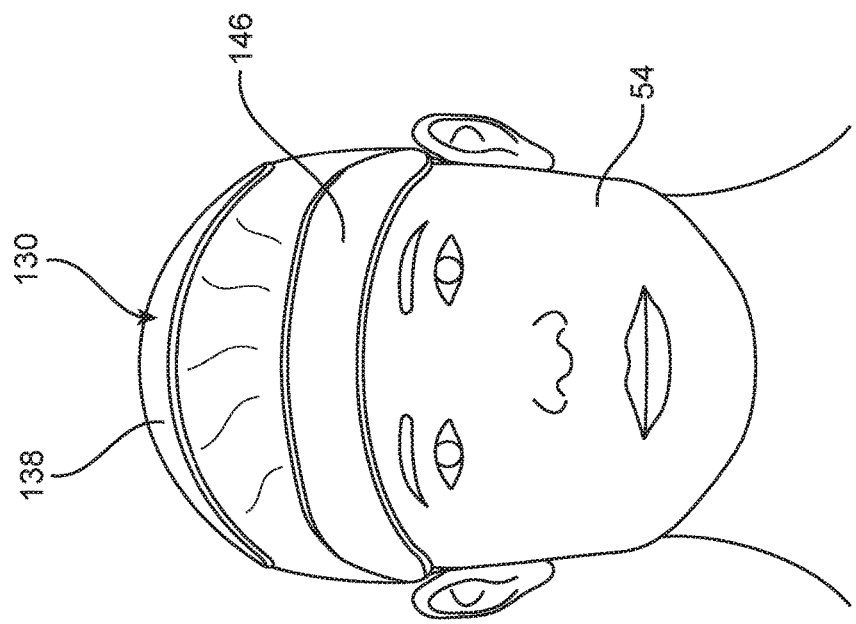
FIG. 12 is a front elevation.
Figure 11:
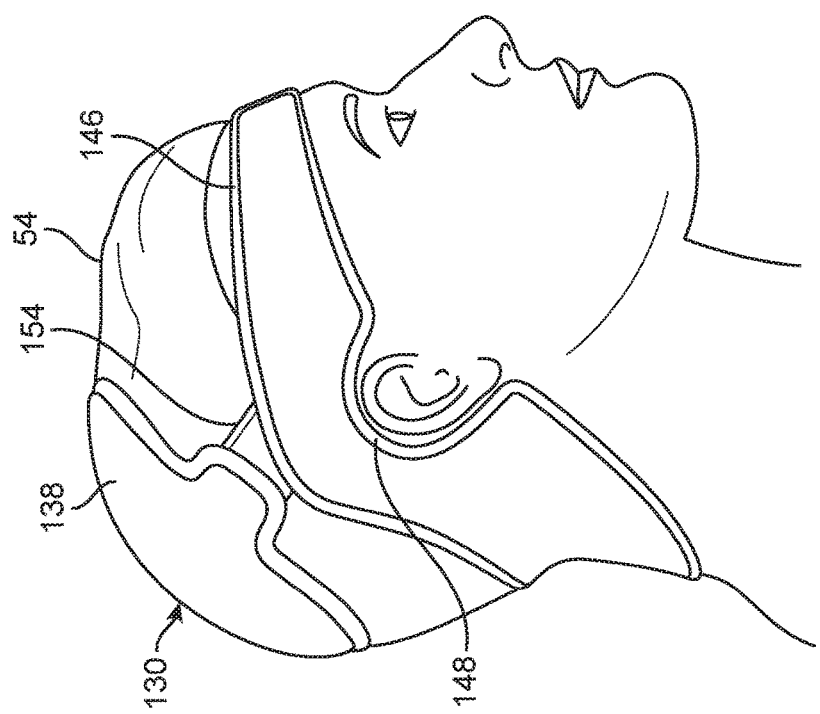
FIG. 11 is a side elevation of a third embodiment.

There is shown in FIGS. 11-12 an alternative embodiment headgear 130 having a first headpiece portion 138 for the crown of the head and a second headpiece portion 146 for the forehead, temples and base of the neck. A cutout portion 148 can be provided for the ear. The first headpiece portion 138 can be connected to the second headpiece portion 146 by an elastomeric connection 154. Cooling members can be connected to inward facing portions of the first head portion 138 and second headpiece portion 146.

Figure 14:
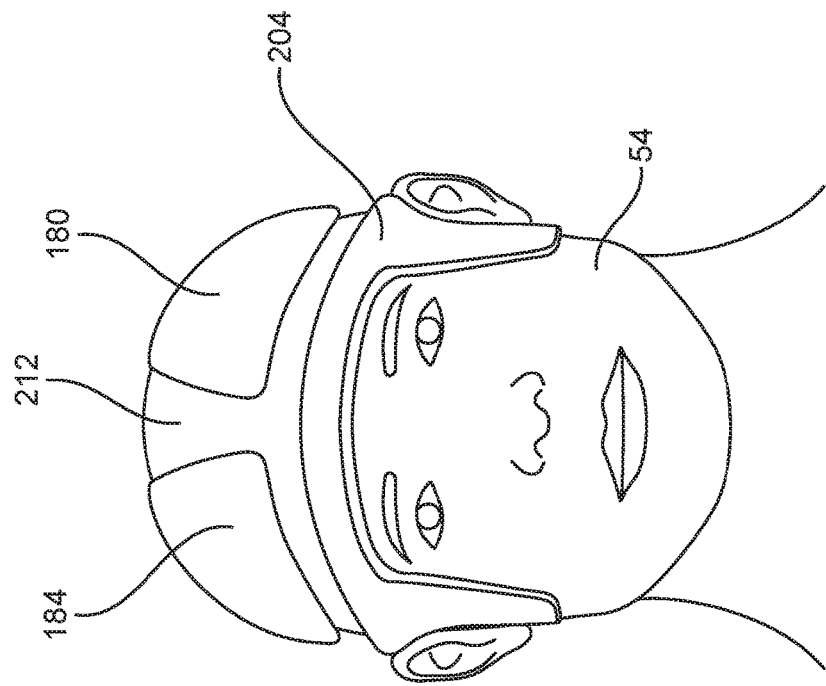
FIG. 14 is a front elevation.
Figure 13:
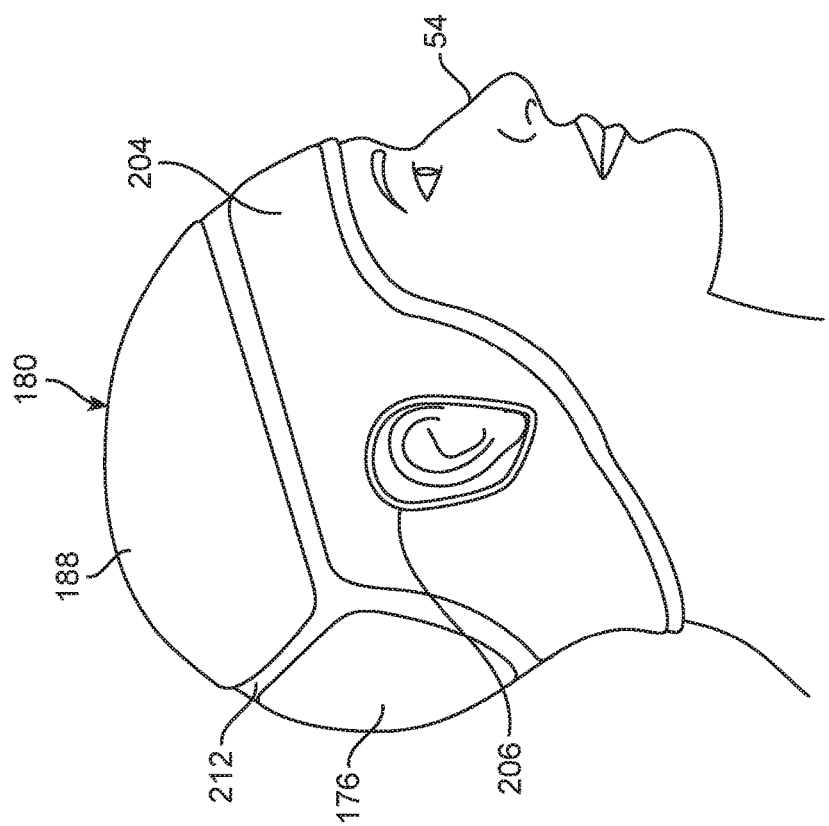
FIG. 13 is a side elevation of a fourth embodiment.

There is shown in FIGS. 13-14 an embodiment of headgear 180 having a headpiece portion 184,188 for the crown of the head, a headpiece portion 196 for the back of the head, and a headpiece portion 204 for the forehead, temples and base of the neck. A cutout 206 can be provided for the ear. The cooling members are connected to an inward surface of the headpiece portions 188, 196 and 204. Elastic portions 212 can be provided to allow the headgear 180 to lie flat during storage and adjustability when placed on the head 54 of the patient.

Figure 16:
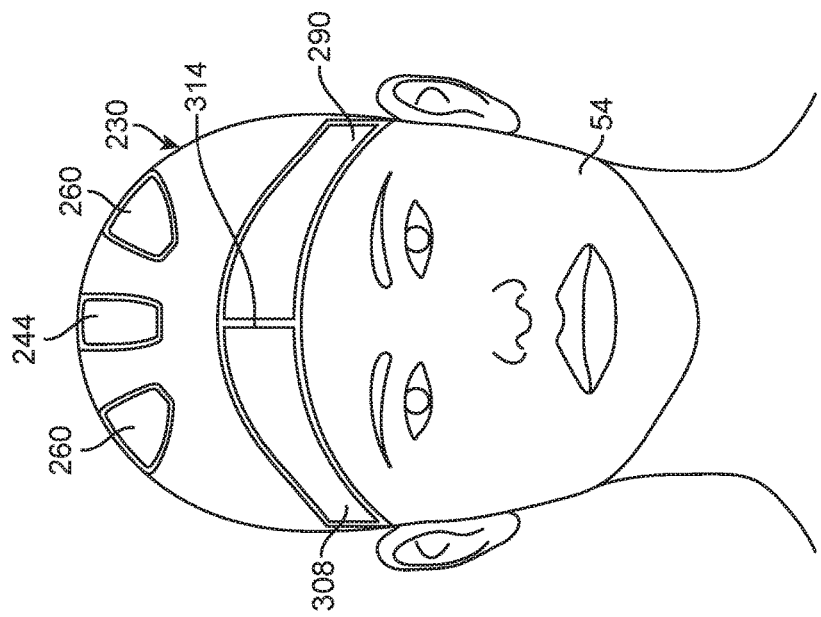
FIG. 16 is a front elevation.
Figure 15:
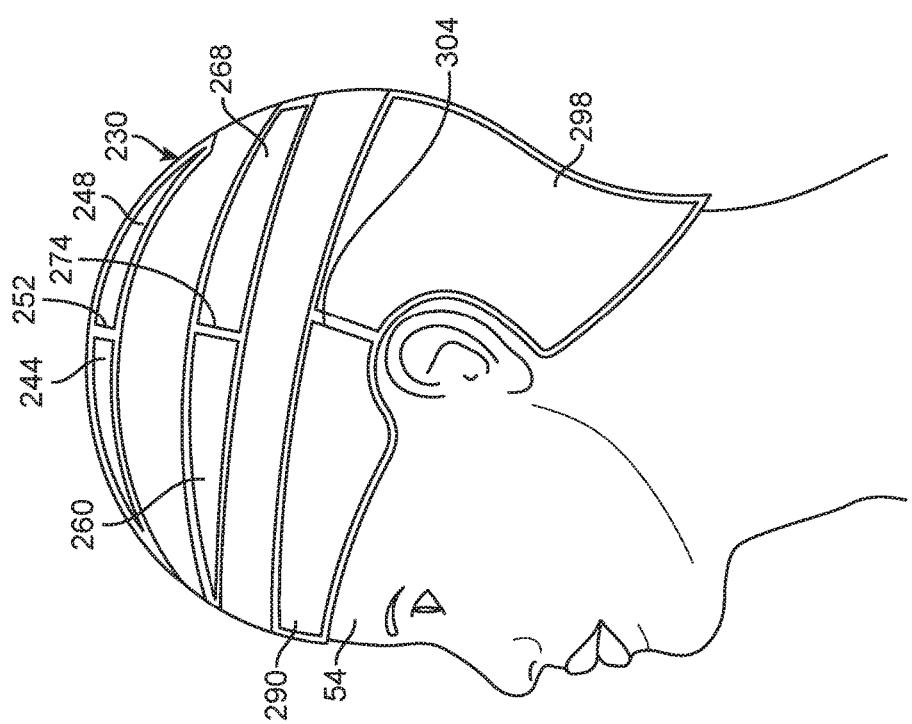
FIG. 15 is a side elevation of a fifth embodiment.

There is shown in FIGS. 15-16 the headgear 230 in which compartments 244 and 248 and dividing member 252 form a cooling member at the crown of the head of the patient 54. Compartments 260, 268 and dividing member 274 form a cooling member on each lateral side of the head. Compartments 290, 308 and dividing member 314 form a cooling member at the forehead. Compartment 298 forms part of cooling member for the base of the neck.

Figure 18:
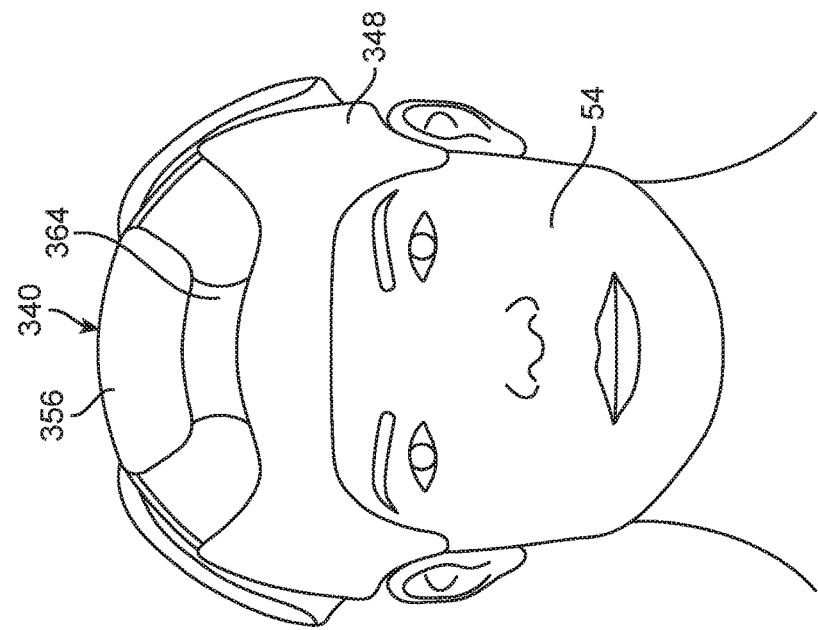
FIG. 18 is a front elevation.
Figure 17:
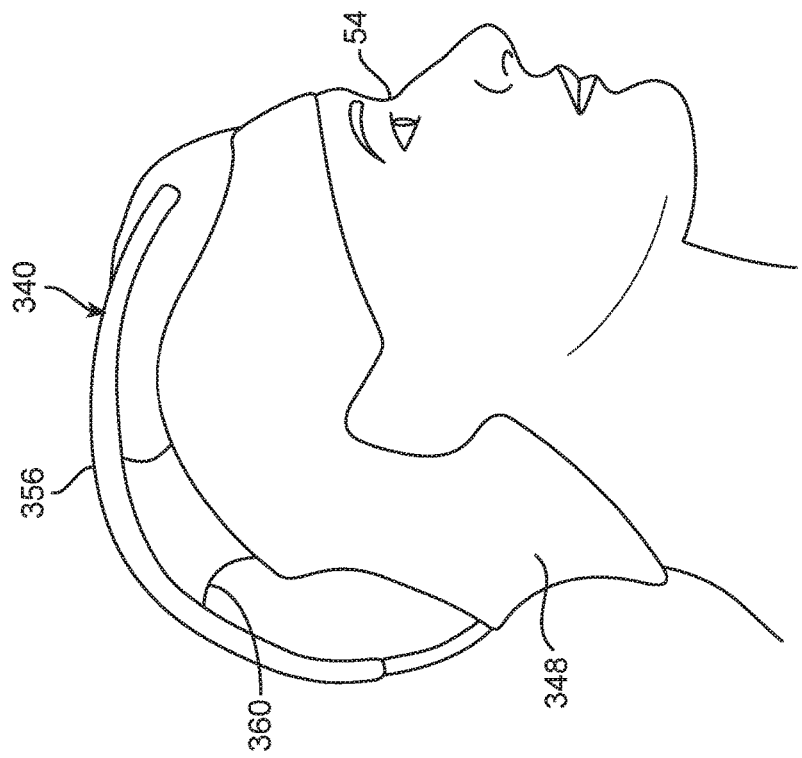
FIG. 17 is a side elevation of a sixth embodiment.
Figure 19:
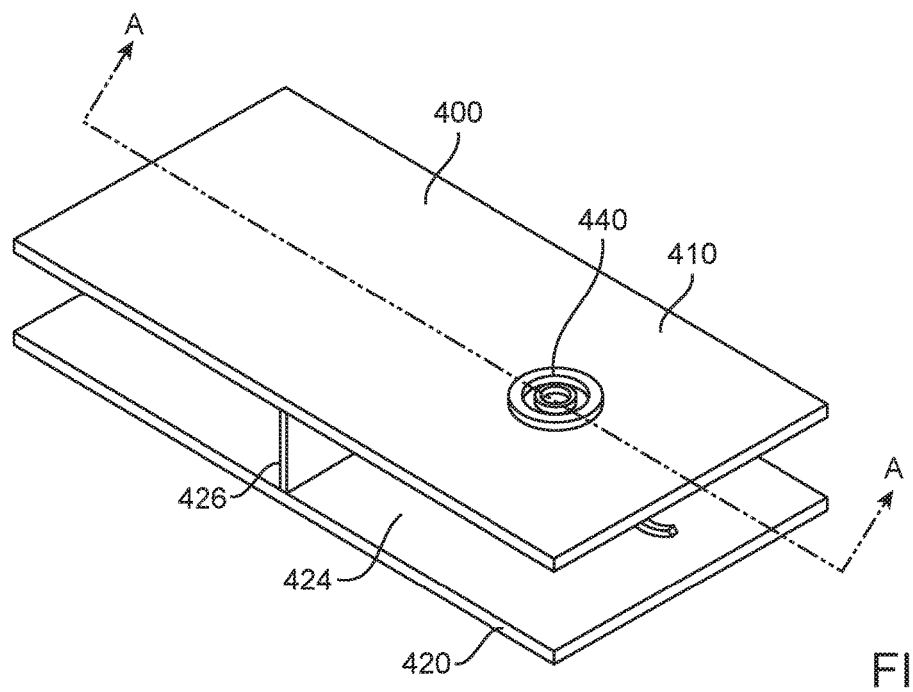
FIG. 19 is a perspective schematic diagram of an alternative cooling member design.
Figure 20:
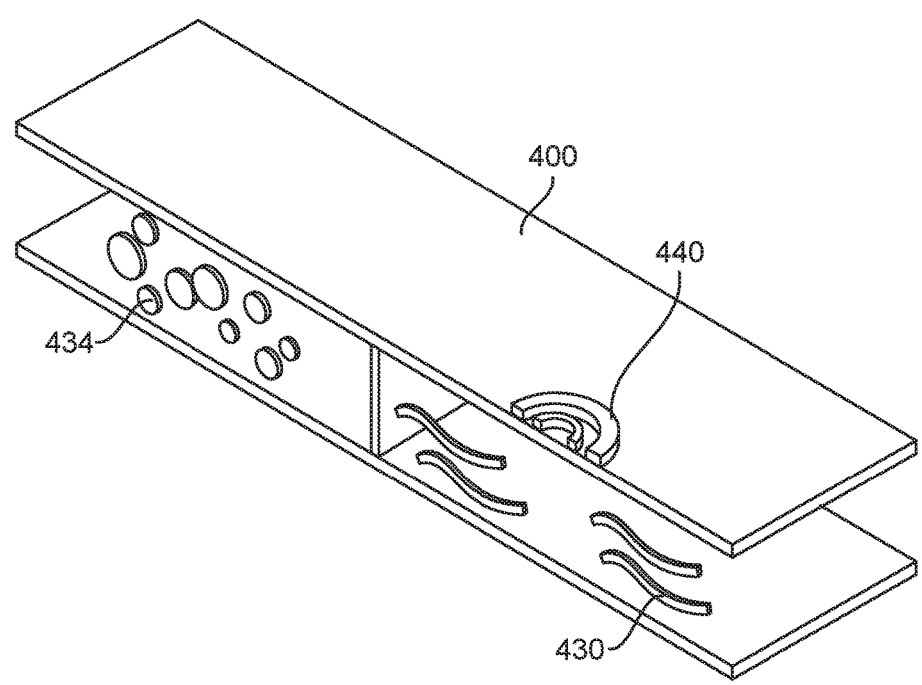
FIG. 20 is a cross section taken along line A-A in FIG. 19.
Figure 21:
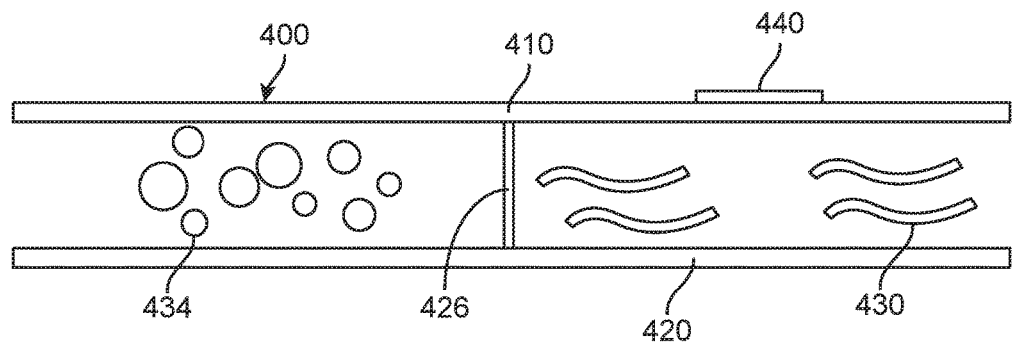
FIG. 21 is a schematic cross-section in a first mode of operation.

There is shown in FIGS. 17-18 a headgear 340 having a headpiece portion 356 for the crown of the head and a headpiece portion 348 for the forehead, temples and base of the neck. The portions can be connected by elastic 360, 364 to provide adjustability in the fit to the head of the patient 54. Cooling members are secured in desired locations on the inward surface of the headpiece portions 356 and 348, as at the forehead, temples, and base of the neck.

Figure 22:
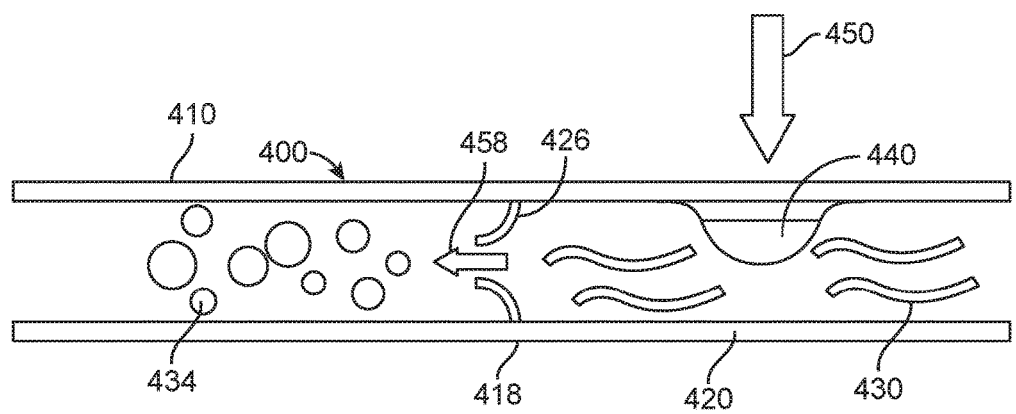
FIG. 22 is a schematic cross-section in a second mode of operation.

There is shown in FIGS. 19-24 an embodiment of cooling member 400 having opposing walls such as exterior wall 410 and interior wall 420 defining an interior space 424 for storing the reaction components. The inward facing surface 418 of the interior wall 420 can be the cooling surface which contact the patient, or can be in thermal contact with the cooling surface. A dividing member 426 separates the space 424 into separate compartments for reaction components such as a water 430 and ammonium nitrate 434. Other reaction components are possible. An activation member is provided for altering the dividing member 426 to permit access between the compartments and mixing of the reaction components. Any suitable activation member is possible. In the embodiment shown, a flexible portion 440 is provided such as a pushbutton. As shown in FIG. 22, when force 450 is applied to the activation member 440 pressure will be applied to water 430 and this pressure will act to rupture the dividing member 426. The dividing member 426 can be constructed to be frangible under the pressures applied by the force 450. Water 430 will be forced into contact with ammonium nitrate 434 through the ruptured dividing member 426 as shown by arrow 458. Mixing of the components will occur throughout both compartments and cooling of the cooling surface 418 will occur.

Figure 23:
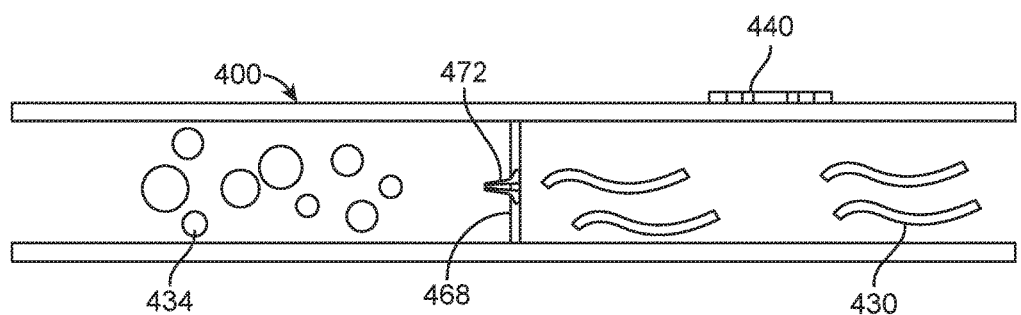
FIG. 23 is a schematic cross-section of a cooling member with a one-way valve, in a first mode of operation.
Figure 24:
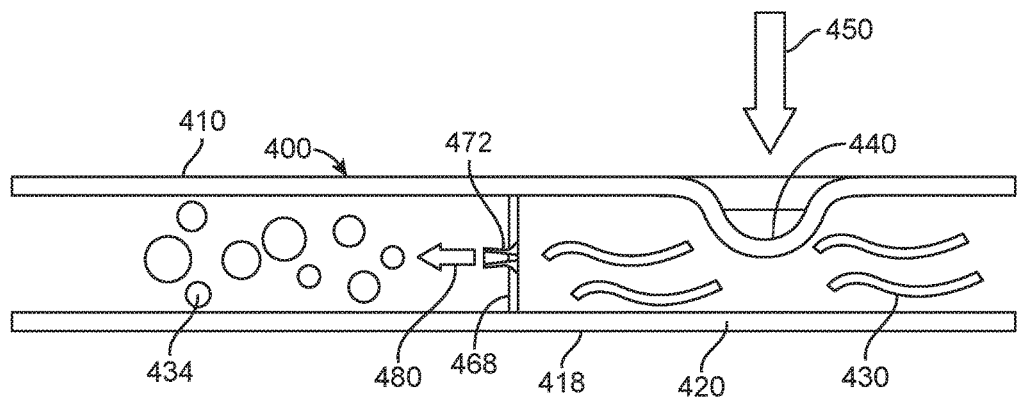
FIG. 24 is a schematic cross-section of the cooling member of FIG. 23, in a second mode of operation.

There is shown in FIGS. 23-24 an embodiment in which the dividing member 468 is fitted with a valve 472 such that pressure applied by force 450 will cause the valve 472 to open and permit the passage of water 430 to contact the ammonium nitrate 434 as indicated by arrow 480. Flow can also occur in the reverse direction through the open valve such that compartments on both sides of the dividing member 468 will be cooled.

Figure 25A:
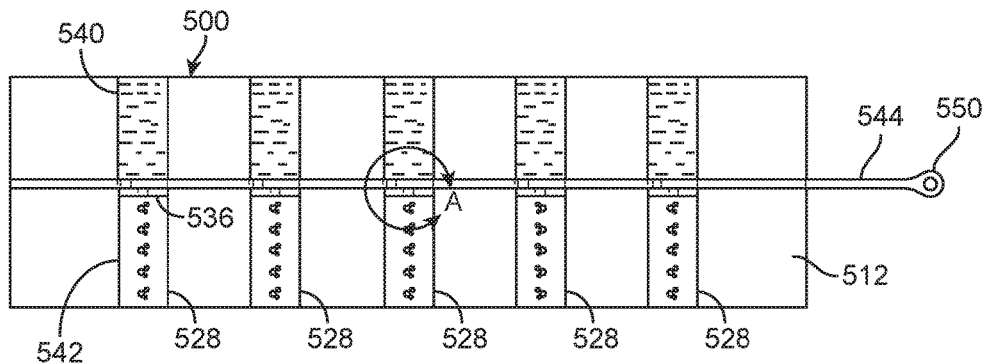
FIGS. 25A and 25B are schematic cross-sections of a plurality of cooling members with a single activation device, in a first mode of operation.
Figure 25B:
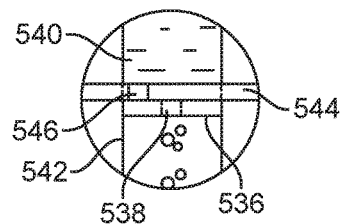
Figure 26A:
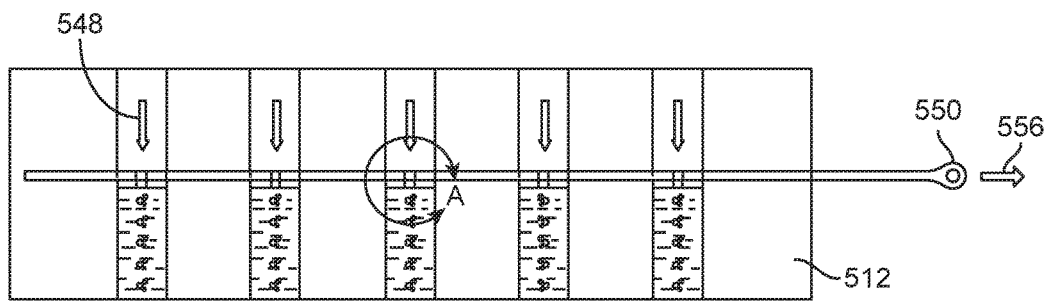
FIGS. 26A and 26B are schematic cross-sections of the cooling members of FIGS. 25A and 25B, in a second mode of operation.
Figure 26B:
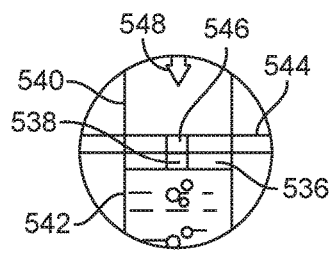
Figure 27:
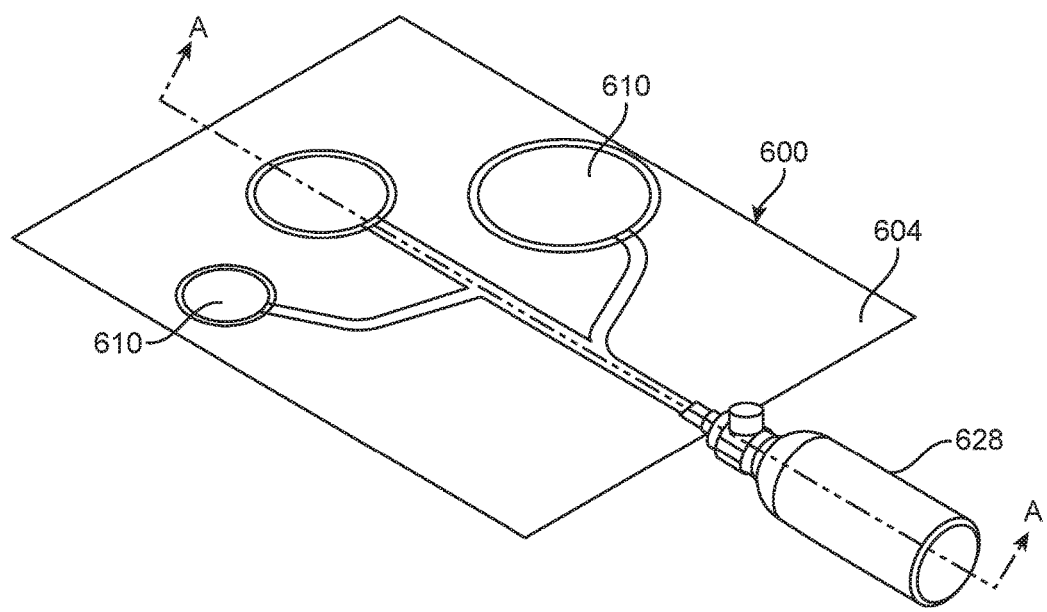
FIG. 27 is a perspective view of an alternative cooling member design.
Figure 28:
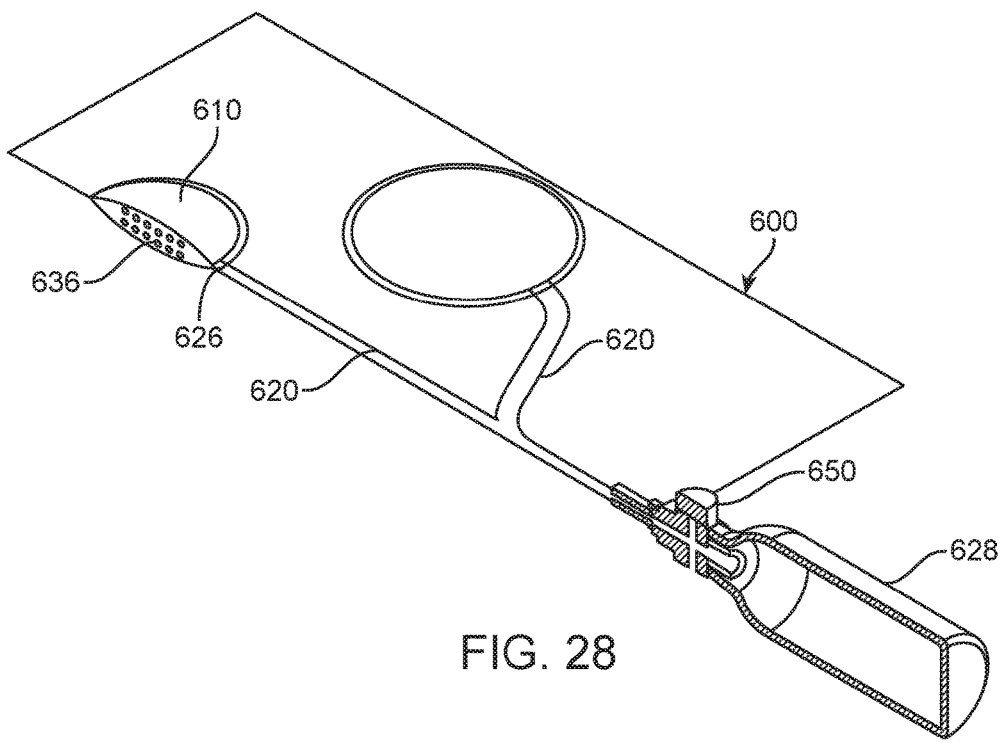
FIG. 28 is a cross-section taken along line A-A in FIG. 27.
Figure 29:
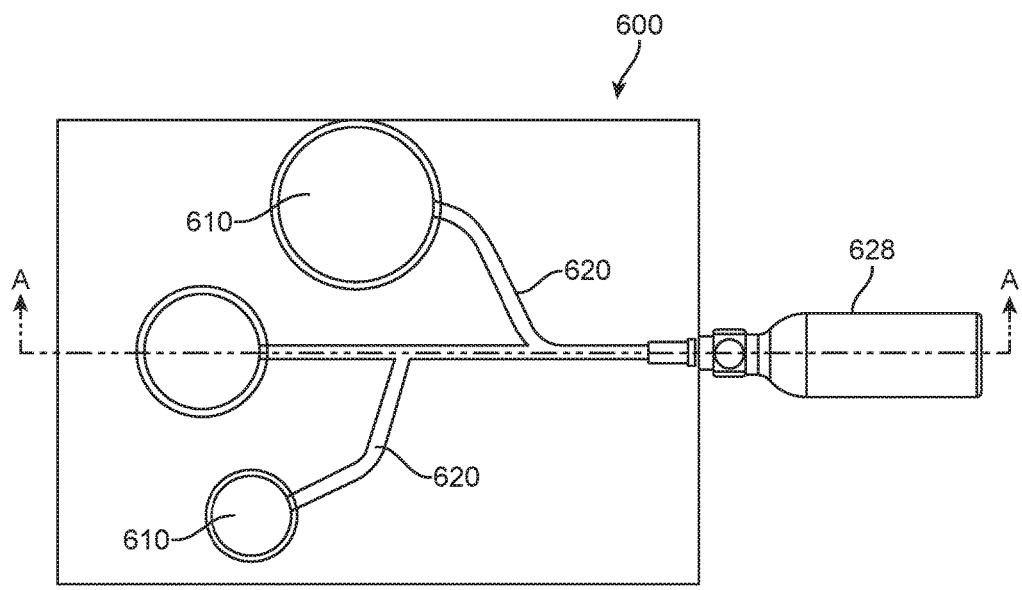
FIG. 29 is a plan view.
Figure 30:
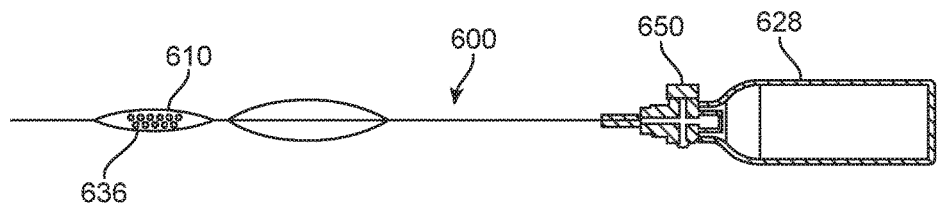
FIG. 30 is a cross-section taken along line A-A in FIG. 29.
Figure 31:
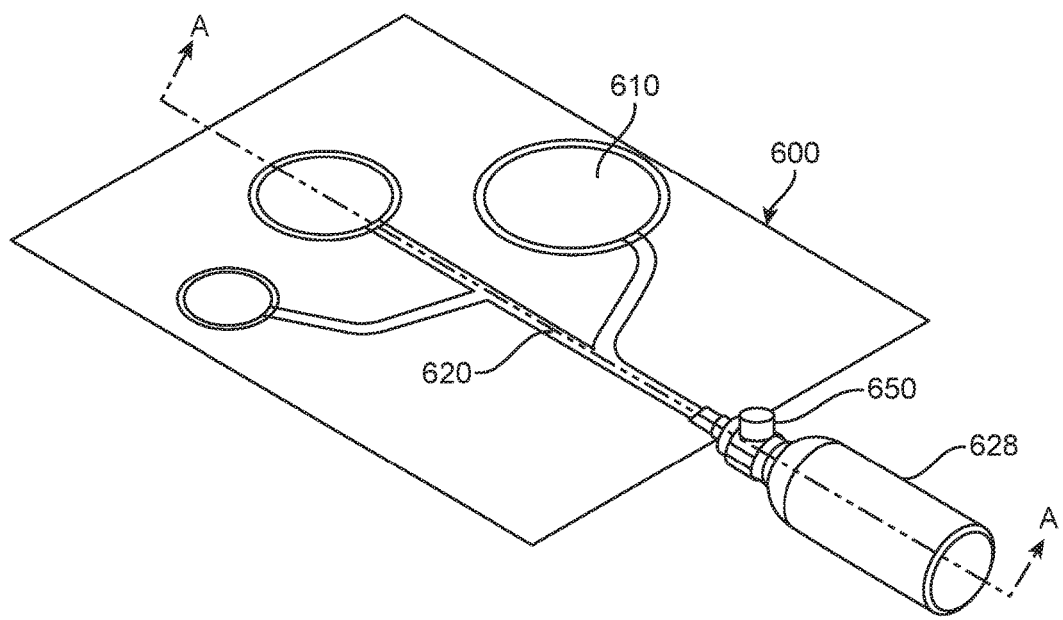
FIG. 31 is a perspective view of the alternative cooling member design of FIG. 27, in a second mode of operation.
Figure 32:
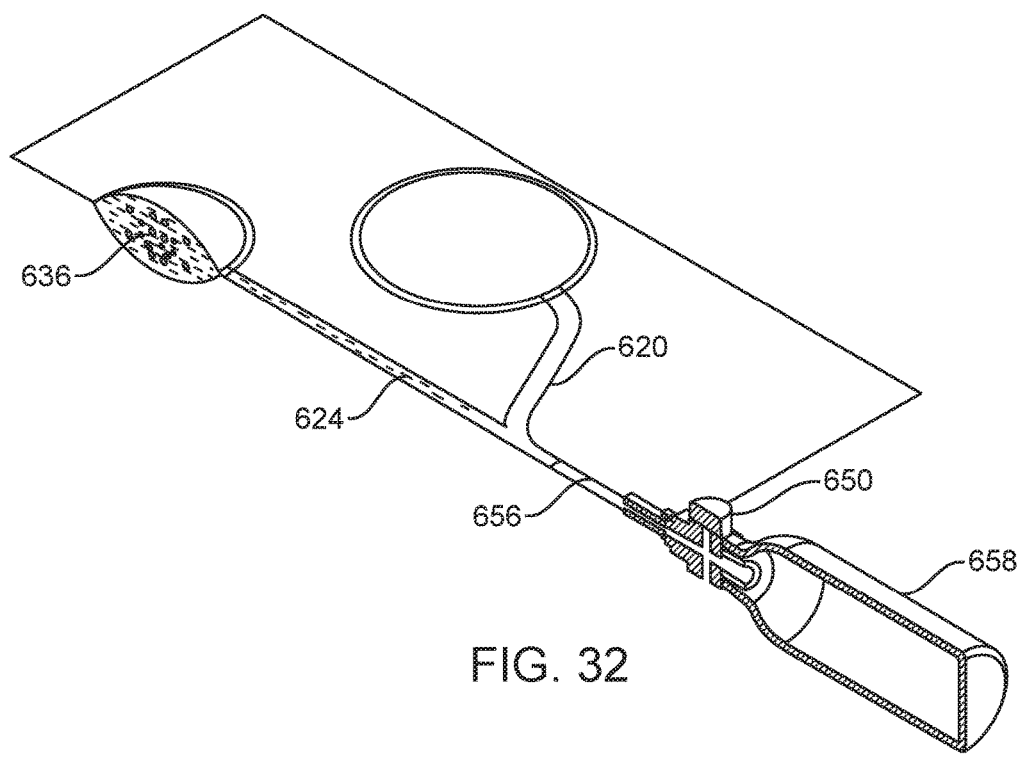
FIG. 32 is a cross-section taken along line A-A in FIG. 31.
Figure 33:
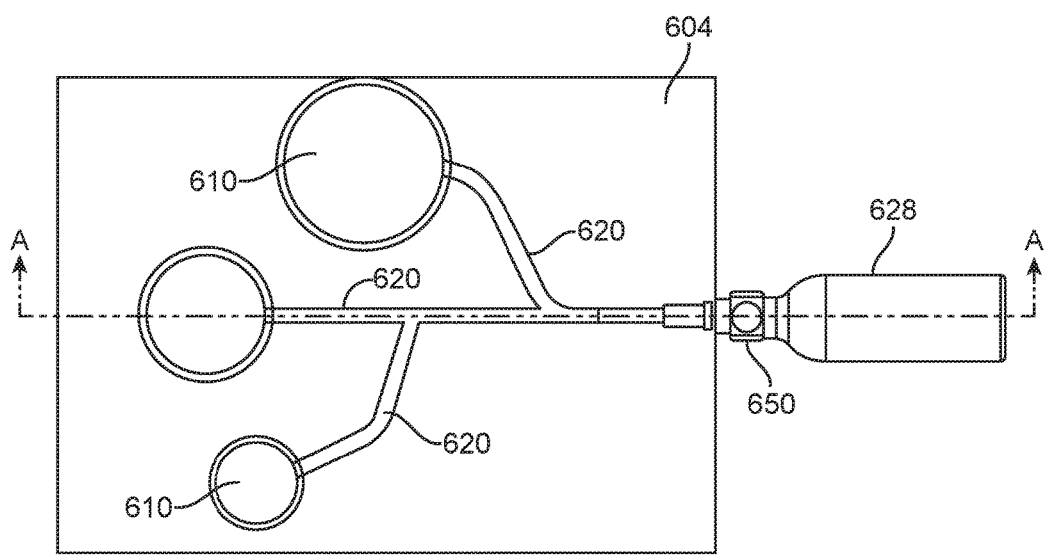
FIG. 33 is a plan view.
Figure 34:
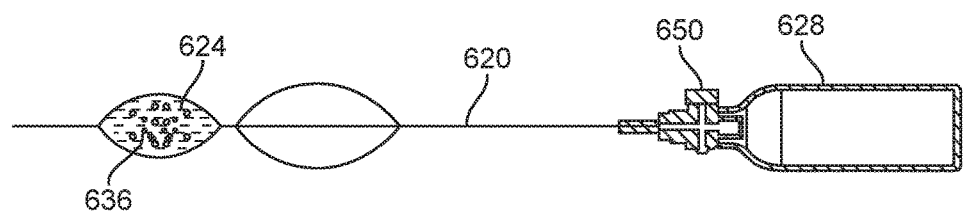
FIG. 34 is a cross-section taken along line A-A in FIG. 33.

There is shown in FIGS. 25-26 a portion 500 of the headpiece having a plurality of cooling members 528 fixed to headpiece 512. The cooling members 528 are shown schematically and can be in a variety of different sizes, shapes and orientations. Cooling members each can have reaction component compartments 540, 542 separated by a dividing member 536 such as a valve, membrane or other suitable construction. The dividing members 536 can have openings 538. A connector 544 can be provided and extends across the cooling members 528 such that a portion of the connector 544 blocks the openings 538 to prevent flow there through. The connector 544 has openings 546 which are initially out of alignment with the openings 538 of the dividing members 536 such that flow between the compartments 540, 542 is not possible (FIG. 25A-B). The connector 544 can be operatively connected to a trigger 550. The trigger 550 is operable in a single manipulation indicated by arrow 556 to move the connector 544 such that the openings 546 of the connector 544 are brought into alignment with the openings 538 of the dividing members 536 such that flow between the compartments 540, 542 is possible as indicated by arrows 548 (FIG. 26A-B). The single manipulation of the trigger 550 by any suitable means will substantially simultaneously provide rapid cooling of all or a plurality of the cooling members 528.

There is shown in FIGS. 27-34 a cooling member 600 having a base portion 604 which can be a portion of the headgear. A plurality of bladders or compartments 610 are distributed throughout the base 604 to provide hypothermic therapy when incorporated into the headgear. One of the reaction components, for example ammonium nitrate 636, can be provided in the bladders 610. The bladders can be closed by a dividing member such as frangible seal 626 or other suitable structure such as a valve. A fluid channel 620 or network of channels communicates with a source of pressurized fluid such as container 628. The container 628 can have within a liquid and pressurized gas, in nature of an aerosol container. Alternatively, the container 628 can include only a pressurized gas and a liquid reaction component such as water can be stored in the fluid channel 620. A valve 650 can be provided to open the container 628 to release pressurized gas or liquid. The container 628 can be other sources of pressurized fluid, such as a syringe type pump or bellows which can be manually operated.

As shown in FIGS. 31-34, the liquid 624 will be driven through the fluid channels 620 by gas 656 to break the seal 626 and fill the bladders or compartments 610 with the liquid. The liquid 624 will mix with the other reaction components, for example ammonium nitrate 636. An endothermic reaction will result, causing the compartments or bladders 610 to cool rapidly and deliver this cooling to the cooling member 600 and the patient.

There is shown in FIGS. 35-36 an embodiment of a cooling member 700 in which a bladder or compartment 710 has been in one of the endothermic reaction components 724. Another compartment such as conduit 716 has stored therein another endothermic reaction component 730. The compartments can be separated by a dividing member 720. A source of pressurized fluid such as container 740 having a suitable valve 748 can be provided to selectively apply pressure to the compartment 716. This will drive the reaction component 730 through the dividing member 720 and into the compartment 710 to mix the endothermic reaction components in cool the cooling member (FIG. 36). Excess fluid 768 can escape the compartment 710 through a suitable check valve 760.

Figure 38A:
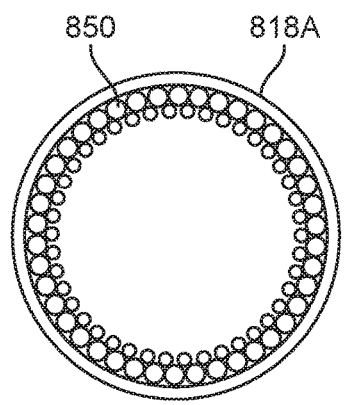
FIGS. 38A and 38B are schematic cross-sections of coded fluid channels of the embodiment of FIGS. 37A, 37B and 37C, in a first mode of operation.
Figure 38B:
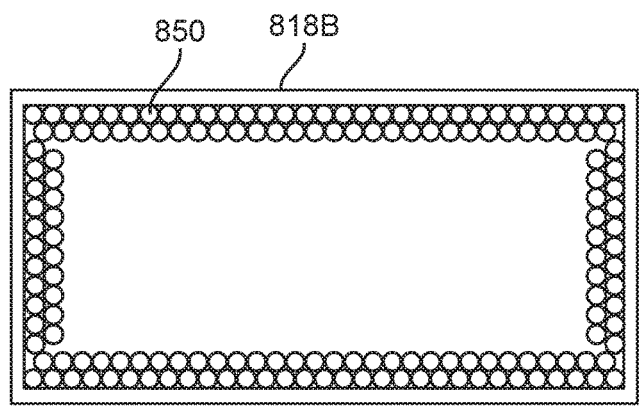
Figure 39A:
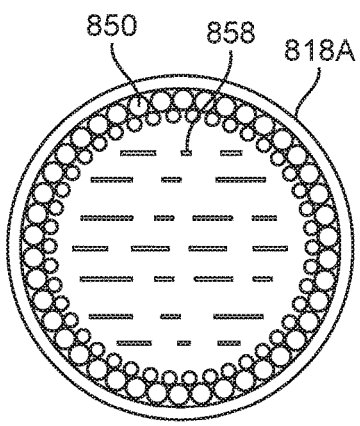
FIGS. 39A and 39B are schematic cross-sections of coated fluid channels of the embodiment of FIG. 37, in a second mode of operation.
Figure 39B:
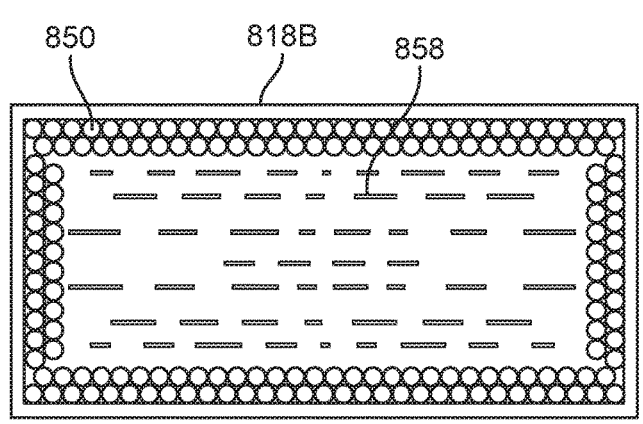

There is shown in FIGS. 37-39 an embodiment in which a headgear 800 has a headpiece 810 with a cooling fluid channel 818 running there through, at least in the locations where cooling of the patient 54 is desired. A supply conduit 826 can be in fluid connection with the cooling fluid channel 818. A source of pressurized fluid such as canister 834 can have a suitable valve 840 control opening of the canister 834.

The fluid channel 818 can be lined with or otherwise contain one of the reaction components, such as the reaction component 850 (FIG. 38A-B). The reaction component 850 can be in solid or semisolid form, such as ammonium nitrate, and can be fixed to the walls of the conduit 818 as shown by a suitable carrier or adhesive or other means. In operation, the valve 840 would be open and the other of the reaction components such as water 858 would be driven into the cooling channels by the pressurization where it would react with the first reaction component 850. The endothermic reaction would cool the cooling channel 818 wherever the first reaction component has been fixed to the walls, and the first reaction component 850 can be preferentially fixed as on one side or the other of the cooling channel 818 two preferentially cool in the desired direction. Other constructions for supplying pressurized fluid are possible, for example a hand pump 846 (FIG. 37B) or bellows (FIG. 37C).

Detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. Hypothermic therapy headgear for patients, comprising:
    a flexible headpiece conforming to the head of the patient for engaging the head of the patient;
    a plurality of cooling members engaged to and distributed about the headpiece for contacting a plurality of surface portions of the patient, the cooling members comprising at least one cooling surface for contacting the surface portion of the patient, and at least two endothermic reaction components, the endothermic reaction components having an initial state where the endothermic reaction components are separated from contact with each other, and a treatment state in which the endothermic reaction components are placed into contact, wherein an endothermic reaction takes place and cools the cooling surface and the corresponding portion of the patient, the cooling members being placed into predetermined positions on the head of the patient when the headpiece is engaged and conforms to the head of the patient;
    an activation device affixed to the headpiece for selectively placing the plurality of endothermic reaction components into the treatment state simultaneously and without external force on the headpiece when a patient is in need of hypothermic therapy;
    wherein the cooling members comprise at least one chamber for at least one of the endothermic reaction components, and a dividing member for separating the endothermic reaction component in the chamber from the at least one other endothermic reaction component, and wherein the activation device is operable to provide access through at least a portion of the dividing member to permit contact between the endothermic reaction components and cooling of the cooling surface and the corresponding portion of the patient; and,
    wherein the activation device comprises a compressed gas container and a valve for opening the container, wherein opening of the valve operates to apply fluid pressure to the dividing member and permits contact of the endothermic reaction components through the dividing member.

2. The hypothermic therapy headgear of claim 1, wherein the headpiece has an adjustable size.

3. The hypothermic therapy headgear of claim 2, wherein the headpiece comprises an elastomeric portion.

4. The hypothermic therapy headgear of claim 2, wherein the headpiece comprises an adjustable closure.

5. The hypothermic therapy headgear of claim 1, wherein the activation device comprises a triggering device for opening a plurality of the dividing members of the cooling members.

6. The hypothermic therapy headgear of claim 5, wherein the triggering device comprises a connector operable to open all of the dividing members with a single manipulation of the connector.

7. The hypothermic therapy headgear of claim 1, wherein a liquid endothermic reaction component is stored in at least one of the chambers, and located in an anterior portion of the cooling member.

8. The hypothermic therapy headgear of claim 1, wherein the compressed gas container is in fluid communication with at least one fluid channel when the valve is opened.

9. The hypothermic therapy headgear of claim 8, wherein one of the endothermic reaction components is provided in the fluid channel, wherein entry of compressed gas from the compressed gas container into the fluid channel will drive that endothermic reaction component through the dividing member and into contact with the other endothermic reaction component in the chamber.

10. The hypothermic therapy headgear of claim 1, further comprising a thermometer for providing an indication of the temperature of at least one of the cooling members.

11. The hypothermic therapy headgear of claim 1, further comprising a timer, the timer being activated by at least one selected from the group consisting of operation of the activation device and a temperature sensor.

12. The hypothermic therapy headgear of claim 1, wherein the endothermic reaction components cool the cooling members to a temperature of less than 15° C. when activated.

13. The hypothermic therapy headgear of claim 1, wherein at least one of the endothermic reaction components comprises ammonium nitrate, and the other of the endothermic reaction components comprises at least one selected from the group consisting of barium hydroxide and water.

14. The hypothermic therapy headgear of claim 1, wherein said headpiece comprises earpieces for locating the headpiece on the users head.

15. The hypothermic therapy headgear of claim 1, wherein the cooling members are positioned on the headgear such that when the headgear is positioned on the head of the patient the cooling members will contact at least one pulse point of the patient.

16. The hypothermic therapy headgear of claim 15, wherein the pulse points comprise at least one selected from the group consisting of the forehead, the base of the neck, and the temples.

17. A method for administering hypothermic therapy to a plurality of surface portions of a patient, comprising the steps of:
    providing a plurality of cooling members comprising at least one cooling surface for contacting the plurality of surface portions of the patient, and at least two endothermic reaction components, the endothermic reaction components having an initial state where the endothermic reaction components are separated from contact with each other, and a treatment state in which the endothermic reaction components are placed into contact, wherein an endothermic reaction takes place and cools the cooling surface and the corresponding portion of the patient; a flexible engagement structure for engaging and conforming to the head of the patient for positioning and retaining the cooling members in contact with the plurality of surface portions of the head of the patient; and an activation device for selectively upon demand placing the endothermic reaction components into the treatment state without external force on the engagement structure, the activation device and the cooling members being affixed to the engagement structure;
    positioning the flexible engagement structure on the head of a patient, whereby engaging and the positioning of the engagement structure on the head will position the cooling members in predetermined positions on the head, and, operating the activation device without external force on the engagement structure to simultaneously place the endothermic reaction components into contact with each other to simultaneously administer hypothermia therapy to the plurality of surface portions of the patient.

* * * * *